United States Patent [19]

Appelbaum et al.

[11] Patent Number: 5,023,180

[45] Date of Patent: Jun. 11, 1991

[54] BRADYRHIZOBIUM JAPONICUM NODULATION REGULATORY PROTEIN AND GENE

[75] Inventors: Edward R. Appelbaum, Madison, Wis.; Hauke Hennecke, Zurich, Switzerland; Joseph W. Lamb, Zurich, Switzerland; Michael Göttfert, Zurich, Switzerland

[73] Assignee: Lubrizol Genetics, Inc., Wickliffe, Ohio

[21] Appl. No.: 61,848

[22] Filed: Jun. 11, 1987

Related U.S. Application Data

[63] Continuation-in-part of Ser. No. 875,297, Jun. 17, 1986, abandoned.

[51] Int. Cl.[5] .................... C12N 15/00; C12N 1/00; C07H 15/12
[52] U.S. Cl. .................... 435/172.3; 435/320.1; 435/878; 935/11; 536/27
[58] Field of Search ............... 435/172.3, 320, 878; 537/26

[56] References Cited

PUBLICATIONS

Downie et al. (1983) Mol. Gen. Genet. 190:359–365.
Kondorosi et al. (1984) Mol. Gen. Genet. 193:445–452.
Downie et al. (1985) Mol. Gen. Genet. 198:255–262.
Innes et al., (1985) Mol. Gen. Genet. 201:426–432.
Kondcrosi et al. (1985) Nitrogen Fixation Research Progress, Evans et al. (eds.) Martinus Nijhoff (Pub.) Dordrecht, The Netherlands, pp. 73–78.
Long et al. (1985) ibid. pp. 87–93.
Downie et al. (1985) ibid. pp. 95–100.
Rolfe et al. (1985) ibid pp. 79–85.
Schofield et al. (1985) ibid P. 125.
Torok et al. (1984) Nucl. Acids Res. 12:9509–9524.
Schofield and Watson (1986) Nucl. Acids Res. 14:2891–2903.
Eglehoff et al. (1985) DNA 4:241–248.
Gottfert et al. (1986) J. Mol. Biol. 191:411–420.
Shearman et al. (1986) EMBO J. 5:647–652.
Fisher et al. (1985) Appl. Environ. Microbiol. 49:1432–1435.
Honma et al. (1985) in Nitrogen Fixation Research Progress, Evans et al. (eds.) Martinus Nijhoff (Pub.), Dordrecht, The Netherlands, p. 120.
Honma and Ausubel (1986) in Molecular Genetics of the Plant—Microbe Interaction, Verma et al. (eds.), Martinus Nijhoff (Pub.) Dordrecht, Netherlands, pp. 223–224.
Kondorosi et al. (1986) ibid pp. 217–222.
Rodriguez—Quinones et al. (1987) Plant Mol. Biol. 8:61–75.
Marvel et al. (1985) Proc. Natl. Acad. Sci. U.S.A. 82:5841–5845.
Noti et al. (1985) Proc. Natl. Acad. Sci. U.S.A. 82:7379–7383.
Russell et al. (1985) J. Bacteriology 164:1301–1308.
Schmidt et al. (1984) EMBO J. 3:1705–1711.
Mulligan and Long (1985) Proc. Natl. Acad. Sci. U.S.A. 82:6609–6613.
Rossen et al. (1985) EMBO J. 4:3369–3373.
Scott (1986) Nucl. Acids Res. 14:2905–2919.
Horvath et al. (1987) EMBO J. 6:841–848.
Appelbaum et al. (1985) in Nitrogen Fixation Research Progress, Evans et al. (eds.) Martinus Nijhoff (Pub.), Dordrecht, The Netherlands, pp. 101–107.
Schofield, Ph.D. Thesis (1984) Australian National University, Canberra, Australia.

Primary Examiner—Elizabeth C. Weimar
Assistant Examiner—David T. Fox
Attorney, Agent, or Firm—Greenlee and Associates

[57] ABSTRACT

Nodulation regulatory genes (nodD genes) of Bradyrhizobium japonicum strains have been isolated and sequenced. Recombinant DNA molecules and vectors containing these regulatory genes are described. These genes, molecules and vectors are useful in the genetic engineering of Rhizobium and Bradyrhizobium strains. A method for selective expression of structural genes in response to the application of chemical factors which induce B. japonicum nod genes which employs these genes is described.

5 Claims, 13 Drawing Sheets

```
 1   AACCATCGTG GCGCGTCTAA TTGCTTTTTC CAAACTTCAG TTTGCTATCC AACCTCCCCC
     TTGGTAGCAC CGCGCAGATT AACGAAAAAG GTTTGAAGTC AAACGATAGG TTGGAGGGGG
                         Cla I
61   AGTTTGGTAA AATCGATTGT TTCGATAGAA CACATCCACA CGATGGATAG ACTCATCAC
     TCAAACCATT TTAGCTAACA AAGCTATCTT GTGTAGGTGT GCTACCTATC TGAGTAGTG
     -------------------------------------------------------------
                 conserved sequence 120  ATG CGG TTC AAG GGA CTT GAT CTA AAT CTT CTC GTT GCG CTC GAC GCC
     TAC GCC AAG TTC CCT GAA CTA GAT TTA GAA GAG CAA CGC GAG CTG CGG
      M   R   F   K   G   L   D   L   N   L   L   V   A   L   D   A
      1                                   10

168  GTG ATG ACG GCG CGC AAC CTC ACA GCG GCG GCT CGC AAA ATC AAT CTG
     CAC TAC TGC CGC GCG TTG GAG TGT CGC CGC CGA GCG TTT TAG TTA GAC
      V   M   T   A   R   N   L   T   A   A   A   R   K   I   N   L
                      20                                  30

216  AGC CAG CCT GCT ATG AGC GCT GCG ATC GCA CGG CTG CGC ACC TAT TTC
     TCG GTC GGA CGA TAC TCG CGA CGC TAG CGT GCC GAC GCG TGG ATA AAG
      S   Q   P   A   M   S   A   A   I   A   R   L   R   T   Y   F
                              40

264  CGC GAT GAA CTC TTT ACT ATG AGA GGT CGC GAA CTC GTC CCG ACA CCT
     GCG CTA CTT GAG AAA TGA TAC TCT CCA GCG CTT GAG CAG GGC TGT GGA
      R   D   E   L   F   T   M   R   G   R   E   L   V   P   T   P
          50                                      60

312  GGC GCG GAA GCG CTT GCA GGT CCG GTT CGC GAG GCC CTG CTG CAC ATC
     CCG CGC CTT CGC GAA CGT CCA GGC CAA GCG CTC CGG GAC GAC GTG TAG
      G   A   E   A   L   A   G   P   V   R   E   A   L   L   H   I
                              70                                  80

360  CAA CTC TCA ATC ATA TCG CGG GAC GCG CTC GAC CCT GCT CAA TCG AGC
     GTT GAG AGT TAG TAT AGC GCC CTG CGC GAG CTG GGA CGA GTT AGC TCG
      Q   L   S   I   I   S   R   D   A   L   D   P   A   Q   S   S
                                          90

408  CGA CGC TTC AGG GTC ATT CTC TCA GAT TTC ATG ACG ATC GTT TTT TTC
     GCT GCG AAG TCC CAG TAA GAG AGT CTA AAG TAC TGC TAG CAA AAA AAG
      R   R   F   R   V   I   L   S   D   F   M   T   I   V   F   F
                          100                                 110

456  CGC AGA ATT GTG GAC CGC ATG GCG CAA GAA GCC CCC GCG GTG CGC TTC
     GCG TCT TAA CAC CTG GCG TAC CGC GTT CTT CGG GGG CGC CAC GCG AAG
      R   R   I   V   D   R   M   A   Q   E   A   P   A   V   R   F
                                      120

504  GAA CTG CTG CCA TTT TCT GAT GAA CCG GAT GAG CTG CTG CGG CGG GGC
     CTT GAC GAC GGT AAA AGA CTA CTT GGC CTA CTC GAC GAC GCC GCC CCG
      E   L   L   P   F   S   D   L   P   D   E   L   L   R   R   G
              130                             *   140

552  GAG GTC GAC TTT CTC ATT CTG CCG GAA CTT TTC ATG TCG AGC GCG CAC
     CTC CAG CTG AAA GAG TAA GAC GGC CTT GAA AAG TAC AGC TCG CGC GTG
      E   A   D   F   L   I   L   P   E   L   r   M   S   S   A   H
                              150                                 160
```

FIG. 3-1

```
600  CCT AAG GCG ACG CTG TTC GAC GAC AGC CTC GTA TGC GTC GGA TGC CGC
     GGA TTC CGC TGC GAC AAG CTG CTC TCG GAG CAT ACG CAG CCT ACG GCG
      P   K   A   T   L   F   D   D   S   L   V   C   V   G   C   R
                                         170

648  GCG AAC AAG CAG CTA TCC CGG CAG CTT ACG TTC GAA CAA TAC ATC TCG
     CGC TTG TTC GTC GAT AGG GCC GTC GAA TGC AAG CTT GTT ATG TAG AGC
      A   N   K   Q   L   S   R   Q   L   T   F   E   Q   Y   I   S
                     180                                 190

696  ATG GGG CAC GTT ACT GCC AGA CGC GGA CGC GCA CTG AGA CCG AAC CTC
     TAC CCC GTG CAA TGA CGG TTC AAG CCT GCG CGT GAC TCT GGC TTG GAG
      M   G   H   V   T   A   R   R   G   R   A   L   R   P   N   L
                                 200

744  GAA GAA TGG TTT TTG CTT GAG CAC GGC CTG AGG AGA CGA ATT GAG GTC
     CTT CTT ACC AAA AAC GAA CTC GTG CCG GAC TCC TCT GCT TAA CTC CAG
      E   E   W   F   L   L   E   H   G   L   R   R   R   I   E   V
             210                                         220

792  GTC GTG CAG GGC TTT AGC CTG ATT CCG CCC CTG TTG CTA GAC ACG AGC
     CAG CAC GTC CCG AAA TCG GAC TAA GGC GGG GAC AAC GAT CTG TGC TCG
      V   V   Q   G   F   S   L   I   P   P   L   L   L   D   T   S
                             230                                 240

840  CGT ATC GGC ACG ATG CCC TTA CGA CTG GCC AGG CAC TTC GAA AAG CGG
     GCA TAG CCG TGC TAC GGG AAT GCT GAC CGG TCC GTG AAG CTT TTC GCC
      R   I   G   T   M   P   L   R   L   A   R   H   F   E   K   R
                                             250

888  ATG CCG TTG CGG ATC ATC CAA CCG CCC CTC CCC CTG CCC ACA TTC ACA
     TAC GGC AAC GCC TAG TAG GTT GGC GGG GAG GGG GAC GGG TGT AAG TGT
      M   P   L   R   I   I   Q   P   P   L   P   L   P   T   F   T
                         260                                 270

936  GAG GCC CTG CAG TGG CCC TCA TTC CAC AAT ACC GAC CCC GCG AGC ATC
     CTC CGG GAC GTC ACC GGG AGT AAG GTG TTA TGG CTG GGG CGC TCG TAG
      E   A   L   Q   W   P   S   F   H   N   T   D   P   A   S   I
                                     280

984  TGG ATG CGT CGG ATA TTG CTC GAG GAA GCA TCC AAC ATG GCA TCT GGG
     ACC TAC GCA GCC TAT AAC GAG CTC CTT CGT AGG TTG TAC CGT AGA CCC
      W   M   R   R   I   L   L   E   G   A   S   N   M   A   S   G
             290                                 300

1032 GAC CAG GAG CCT CCA ACT CGC AGG CGG TGT TAGGCTTAC CTTAAGCTGG
     CTG GTC CTC GGA GGT TGA GCG TCC GCG ACA ATCCGAATG GAATTCGACG
      D   Q   E   P   P   T   R   R   R   C
                             310

1081 GCTCTGAACA TCCCCGGCAC ACTGTAGAAC CTTCGACGTG CCCCGTTTTC
     CGAGACTTGT AGGGGCCGTG TGACATCTTG GAAGCTGCAC GGGGCAAAAG
```

FIG. 3-2

```
       -120
5'... TCCTTTCCCG   GGCGCAGGAA   TGAGCCGATG   TCCATTGGGG
      AGGAAAGGGC   CCGCGTCCTT   ACTCGGCTAC   AGGTAACCCC

-80
      CGGGCCAAGA   CGATTGCTCC   AGGCGCTGGC   GCCACCGCAC
      GCCCGGTTCT   GCTAACGAGG   TCCGCGACCG   CGGTGGCGTG

-40
      GCTATTGCGC   AGCAACGACG   TTTGTGCCGG   ATAGGAAGAG
      CGATAACGCG   TCGTTGCTGC   AAACACGGCC   TATCCTTCTC
```

```
  1                                                      30
ATG   CGT   TTC   AAA   GGT   CTG   GAT   CTA   AAT   CTT
TAC   GCA   AAG   TTT   CCA   GAC   CTA   GAT   TTA   GAA
 M     R     F     K     G     L     D     L     N     L
 1                                                       10

60
CTG   GTC   GCG   CTG   GAT   GCT   CTA   ATA   ACT   GAG
GAC   CAG   CGC   GAC   CTA   CGA   GAT   TAT   TGA   CTC
 L     V     A     L     D     A     L     I     T     E
                                                         20

90
CGC   AAC   CTC   TCG   TCA   GCC   GCA   CGC   AAG   ATC
GCG   TTG   GAG   AGC   AGT   CGG   CGT   GCG   TTC   TAG
 R     N     L     S     S     A     A     R     K     I
                                                         30

120
AAT   CTT   AGT   CAG   CCG   GCA   ATG   AGC   GCA   GCC
TTA   GAA   TCA   GTC   GGC   CGT   TAC   TCG   CGT   CGG
 N     L     S     Q     P     A     M     S     A     A
                                                         40

150
GTT   GCC   CGG   CTG   CGC   AAG   CAT   TTC   CGT   GAT
CAA   CGG   GCC   GAC   GCG   TTC   GTA   AAG   GCA   CTA
 V     A     R     L     R     K     H     F     R     D
                                                         50

180
GAA   ATG   TTT   GGA   ATG   AGG   GGG   CGC   GAA   CTT
CTT   TAC   AAA   CCT   TAC   TCC   CCC   GCG   CTT   GAA
 E     M     F     G     M     R     G     R     E     L
                                                         60

210
GTC   TTG   AGC   TCA   CGC   GCG   GAA   GGG   CTC   GCG
CAG   AAC   TCG   AGT   GCG   CGC   CTT   CCC   GAG   CGC
 V     L     S     S     R     A     E     G     L     A
                                                         70
```

FIG. 4-1

```
                                                                    240
GCT  CCT  GTG  CGC  GAG  GCT  CTG  ATG  CAC  ATT
CGA  GGA  CAC  GCG  CTC  CGA  GAC  TAC  GTG  TAA
 A    P    V    R    E    A    L    M    H    I
                                                                     80

270
GAA  CTC  TCG  ATT  ATG  GCC  CGA  CAT  CCG  TTC
CTT  GAG  AGC  TAA  TAC  CGG  GCT  GTA  GGC  AAG
 E    L    S    I    M    A    R    H    P    F
                                                                     90

300
GAC  CCA  GCT  CGA  TTG  AAC  CGC  CGA  TTC  AGG
CTG  GGT  CGA  GCT  AAC  TTG  GCG  GCT  AAG  TCC
 D    P    A    R    L    N    R    R    F    R
                                                                    100

330
ATC  GTC  CTT  TCT  GAC  TTC  GTA  ACA  GTT  GTG
TAG  CAG  GAA  AGA  CTG  AAG  CAT  TGT  CAA  CAC
 I    V    L    S    D    F    V    T    V    V
                                                                    110

360
CTC  TTC  CGA  AAT  GTC  GTA  GCA  CGC  GTC  AGC
GAG  AAG  GCT  TTA  CAG  CAT  CGT  GCG  CAG  TCG
 L    F    R    N    V    V    A    R    V    T
                                                                    120

390
CGA  GAA  GCC  CCC  GCC  GTC  AGC  TTC  GAA  TTG
GCT  CTT  CGG  GGG  CGG  CAG  TCG  AAG  CTT  AAC
 R    E    A    P    A    V    S    F    E    L
                                                                    130

420
GCT  GCG  CCG  ACC  GAT  AGG  CAC  GAG  CTG  CTC
CGA  CGC  GGC  TGG  CTA  TCC  GTG  CTC  GAC  GAG
 A    A    P    T    D    E    H    E    L    L
                                                                    140

450
CTC  CGC  CGC  GGT  GAA  GTC  GAT  TTT  GTT  ATC
GAG  GCG  GCG  CCA  CTT  CAG  CTA  AAA  CAA  TAG
 L    R    R    G    E    V    D    F    V    I
                                                                    150

480
CGG  CCA  GAT  TTT  TTC  ATG  TCC  AGC  ACG  CAC
GCC  GGT  CTA  AAA  AAG  TAC  AGG  TCG  TGC  GTG
 R    P    D    F    F    M    S    S    T    H
                                                                    160

510
CCC  AGA  GCG  GCC  CTA  TTC  GAG  GAG  CGA  CTC
GGG  TCT  CGC  CGG  GAT  AAG  CTC  CTC  GCT  GAG
 P    R    A    A    L    F    E    E    R    L
                                                                    170
```

FIG. 4-2

```
                                                        540
GTC  TGC  GTA  GGC  TGC  TGC  ACC  AAT  AGG  GAA
CAG  ACG  CAT  CCG  ACG  ACG  TGG  TTA  TCC  CTT
 V    C    V    G    C    C    T    N    R    E
                                               180

570
TTA  CAA  CCC  CGG  CTT  ACA  TTC  GAT  CGA  TAT
AAT  GTT  GGG  GCC  GAA  TGT  AAG  CTA  GCT  ATA
 L    Q    P    R    L    T    F    D    R    Y
                                               190

600
ATG  TCG  ATG  GGT  CAC  GTT  GCA  GTT  AAG  CAC
TAC  AGC  TAC  CCA  GTG  CAA  CGT  CAA  TTC  GTG
 M    S    M    G    H    V    A    V    K    H
                                               200

630
GGA  GGT  GCG  CCC  CGG  ACG  CCA  GTT  GAG  CAT
CCT  CCA  CGC  GGG  GCC  TGC  GGT  CAA  CTC  GTA
 G    G    A    P    R    T    P    V    E    H
                                               210

660
TCC  TTT  TTG  ACT  GAT  CTC  GGA  CCC  ACG  CGG
AGG  AAA  AAC  TGA  CTA  GAG  CCT  GGG  TGC  GCC
 S    F    L    T    D    L    G    P    T    R
                                               220

690
CGC  ATC  GAC  ATC  CTC  GTG  CAG  AGC  TTC  AGC
GCG  TAG  CTG  TAG  GAG  CAC  GTC  TCG  AAG  TCG
 R    I    D    I    L    V    Q    S    F    S
                                               230

720
ATG  ATC  CCG  CCT  CTC  ATA  GTT  GGG  ACG  AAC
TAC  TAG  GGC  GGA  GAG  TAT  CAA  CCC  TGC  TTG
 M    I    P    P    L    I    V    G    T    N
                                               240

750
CGC  ATA  GGC  ACG  ATG  CCA  TTA  GGG  CTC  GTG
GCG  TAT  CCG  TGC  TAC  GGT  AAT  CCC  GAG  CAC
 R    I    G    T    M    P    L    G    L    V
                                               250

780
AGG  CAT  TTC  CAA  AGA  ACG  ATG  CCC  CTT  CGG
TCC  GTA  AAG  GTT  TCT  TGC  TAC  GGG  GAA  GCC
 R    H    F    Q    R    T    M    P    L    R
                                               260

810
ATC  GTT  GAG  CTT  CCG  CAT  CCA  TTC  CCC  GCC
TAG  CAA  CTC  GAA  GGC  GTA  GGT  AAG  GGG  CGG
 I    V    E    L    P    H    P    F    P    A
                                               270
```

FIG. 4-3

```
                                                            840
TTC  ACC  GAG  GCG  GTC  CAA  TGG  CCC  TCA  CTT
AAG  TGG  CTC  CGC  CAG  GTT  ACC  GGG  AGT  GAA
 F    T    E    A    V    Q    W    P    S    L
                                                  280

870
CAC  AAC  AGC  GAC  CCG  GGA  AGT  CTG  TGG  ATG
GTG  TTG  TCG  CTG  GGC  CCT  TCA  GAC  ACC  TAC
 H    N    S    D    P    G    S    L    W    M
                                                  290

900
AGG  GAC  ATT  TTG  TTT  CAG  GAG  GCC  ACC  CGC
TCC  CTG  TAA  AAC  AAA  GTC  CTC  CGG  TGG  GCG
 R    D    I    L    F    Q    E    A    T    R
                                                  300

930
ATG  GCA  ACT  ACA  CAA  GAG  CTC  CGT  GTG  ACC
TAC  CGT  TGA  TGT  GTT  CTC  GAG  GCA  CAC  TGG
 M    A    T    T    Q    E    L    R    V    T
                                                  310

960
AGC  AGC  CCG  GAA  GAC  GCG  GAG  CCC  CCG  GGA
TCG  TCG  GGC  CTT  CTG  CGC  CTC  GGG  GGC  CCT
 S    S    P    E    D    A    E    P    P    G
                                                  320

990
CAT  TTC  GTG  CGA  TCC  GTC  TCA  CCG  TTG  CCG
GTA  AAG  CAC  GCT  AGG  CAG  AGT  GGC  AAC  GGC
 H    F    V    R    S    V    S    P    L    P
                                                  330

1038
TAA  GCACATTCGCGAAGTTACGAACCTCACATTCCCAACACTTGTCTC
ATT  CGTGTAAGCGCTTCAATGCTTGGAGTGTAAGGGTTGTGAACAGAG
 *

1070
AACACACAATTCCTGCTCGCCTGGCTTGCTCT
TTGTGTTAAGGACGAGCGGACCGAACGAGA...3'
```

BRADYRHIZOBIUM JAPONICUM NODULATION REGULATORY PROTEIN AND GENE

This application is a continuation-in-part of application Ser. No. 875,297, filed June 17, 1986, now abandoned.

FIELD OF THE INVENTION

The present invention relates in general to the field of legume-Rhizobium symbiosis, and in particular to the isolation and sequencing of regulatory genes in *Bradyrhizobium japonicum* strains which are required for the induction of expression of rhizobial nodulation genes.

BACKGROUND OF THE INVENTION

Soil bacteria of the genus Rhizobium, a member of the family Rhizobiaceae, are capable of infecting plants and inducing a highly differentiated structure, the root nodule, within which atmospheric nitrogen is reduced to ammonia by the bacteria. The host plant is most often of the family Leguminosa. Previously, Rhizobium species were informally classified in two groups, either as "fast-growing" or "slow-growing" to reflect the relative growth rates in culture. The group of "slow-growing" rhizobia has recently been reclassified as a new genus, Bradyrhizobium (Jordan, D.C. (1982) International Journal of Systematic Bacteriology 32:136). The fast-growing rhizobia include *Rhizobium trifolii, R. meliloti, R. leguminosarum* and *R. phaseolus*. These strains generally display a narrow host range. Fast-growing *R. japonicum* which nodulate wild soybeans, *Glycine max* cv. Peking and siratro, and fast-growing members of the cowpea *Rhizobium* display broader host range. *R. japonicum* strains form only ineffective nodules on commercial soybean cultivars. The fast-growing *R. japonicum* strains are now designated *R. fredii* (Scholla and Elkan (1984) Int'l. Journal Systematic Bacteriol. 34:484-486). The slow-growing *Bradyrhizobium* include the commercially important soybean nodulating strains *Bradyrhizobium japonicum* (i.e., USDA 110 and USDA 23), the symbiotically promiscuous rhizobia of the "cowpea group", including Bradyrhizobium sp. (Vigna) and Bradyrhizobium sp. Parasponia (formerly *Parasponia Rhizobium*) which nodulates the non-legume Parasponia, as well as a number of tropical legumes including cowpea and siratro. Within the species *B. japonicum*, a number of distinct serogroups represented by USDA110 and USDA123, for example, are recognized. Strains belonging to a serogroup have been found to display quantitatively different nodulation or symbiotic properties when compared to strains of other serogroups. For example, *B. japonicum* USDA110 are more effective for nitrogen fixation than USDA123 strains, but USDA123 strains appear to be more competitive for infection and nodule occupancy when compared to USDA110 strains.

Nodulation and development of effective symbiosis is a complex process requiring both bacterial and plant genes. Several recent reviews of the genetics of the Rhizobium-legume interaction are found in Broughton, W.J., ed. (1982) *Nitrogen Fixation*. Volumes 2 and 3 (Clarendon Press, Oxford); Puhler, A. ed. (1983) *Molecular Genetics of the Bacteria-Plant Interaction* (Springer-Verlag, Berlin); Szalay, A.A. and Leglocki, R.P., eds. (1985) *Advances in Molecular Genetics of the Bacteria-Plant Interaction* (Cornell University Publishers, Ithaca, New York); Long, S.R. (1984) in *Plant Microbe Interactions* Volume 1, Kosuge, T. and Nester, E.W. eds. (McMillan, New York) pp. 265-306; and Verma, D.P.S. and Long, S.L. (1983) International Review of Cytology (Suppl. 14), Jeon, K.W. (ed.), Academic Press, p. 211-245.

In the fast-growing species, the genes required for nodulation and nitrogen fixation are located on large Sym (symbiotic) plasmids. Although the process of recognition, infection and nodule development is complex, it appears that at least for the fast-growing rhizobia relatively few bacterial genes are directly involved and these are closely linked on the Sym plasmid. For example, a 14 kb fragment of the *Rhizobium trifolii* Sym plasmid is sufficient to confer clover-specific nodulation upon a Rhizobium strain cured of its Sym plasmid, as well as on an Aorobacterium strain which does not normally nodulate plants (Schofield et al., (1984) Plant Mol. Biol. 3:3-11). Nodulation and nitrogenase genes are also localized on symbiotic plasmids in *R. leguminosarum* (Downie et al. (1983) Mol. Gen. Genet. 190:359-365) and in *R. meliloti* (Kondorosi et al. (1984) Mol. Gen. Genet. 193:445-452).

Fine structure genetic mapping has been used to locate individual nodulation genes in fast-growing rhizobia. Transposon mutagenesis, most often using the transposon Tn5, has identified about 10 nodulation genes associated with non-nodulation, delayed nodulation and altered host range phenotypes (Djordjevic et al. (1985) Mol. Gen. Genet. 200:263-271; Downie et al. (1985) Mol. Gen. Genet. 198:255-262; Kondorosi et al., 1984; Innes et al. (1985) Mol Gen. Genet. 201:426-432; Kondorosi et al. (1985) *Nitrogen Fixation Research Progress,* Evans et al. (eds.) Martinus Nijhoff, Dordrecht, Netherlands, pp. 73-78; Long et al. (1985) ibid., pp. 87-93; Downie et al. (1985) ibid., pp. 95-100; Rolfe et al. (1985) ibid., pp. 79-85; Schofield and Watson (1985) ibid., p. 125).

Three "common" Sym plasmid encoded nodulation genes have been identified in *R. meliloti* (Torok et al. (1984) Nucleic Acids Res. 12:9509-9524; Jacobs et al. (1985) J. Bacteriol. 162:469-476), *R. leguminosarum* (Rossen et al. 1984) Nucleic Acids Res. 12:9497-9508) and *R. trifolii* (Schofield and Watson (1986) Nucleic Acids Res. 14:2891-2903; Rolfe et al. (1985) *Nitrogen Fixation Research Progress,* Evans et al. (eds.), Martinus Nijhoff, p. 79-85; Schofield and Watson, ibid., p. 125; Schofield Ph.D. Thesis (1984) Australian National University, Canberra, Australia). These genes, designated *nod*A, B and C, are associated with the early stages of infection and nodulation and are functionally and structurally conserved among fast-growing rhizobia. In *R. meliloti, R. leguminosarum* and *R. trifolii,* the *nod*A B and C genes are organized in a similar manner and are believed to be coordinately transcribed as a single genetic operon. Bacteria having mutations in these genes fail to induce visible nodules on host legumes (nod−) and in some cases even fail to induce root hair curling (hac−) which is prerequisite for infection. The DNA region adjacent to *nod*A (5'- from the start of *nod*A) in *R. meliloti* was reported to be involved in early nodulation function (Torok et al., 1984). The region adjacent to the *nod*ABC operon in fast-growing rhizobia has been shown to contain an open reading frame, designated *nod*D. Homologous, similarly located *nod*D genes have been identified and sequenced in *R. meliloti* (Eglehoff et al. (1985) DNA 4:241-248; Gottfert et al. (1986) J. Mol. Biol. 191:411-420), *R. leguminosarum* (Shearman et al. (1986) EMBO J. 5:647-652; Downie et al.

(1985) Mol. Gen. Genet. 198:255-262) and *R. trifolii* (Schofield and Watson, 1985 and 1986; Rolfe et al., 1985; Schofield, 1984). Mutations in *nod*D of R. meliloti are reported to be complemented by the *nod*D gene of *R. trifolii* (Fisher et al. (1985) Applied Environ. Microbiology 49:1432-1435). Comparison of the DNA sequences of *nod*D genes and the deduced amino acid sequences of the *nod*D proteins confirm the existence of significant sequence conservation of these genes among fast-growing rhizobia.

*Nod*D mutants of the various Rhizobium strains do not, however, display the same nodulation phenotypes. *Nod*D mutants of *R. leguminosarum* (Downie et al. (1985) Mol. Gen. Genet. 198:255-262) and *R. trifolii* (Schofield et al. (1983) Mol. Gen. Genet. 192:459-465) are reported to display unequivocal Nod− phenotypes. In contrast, *R. meliloti nod*D mutants are reported to have either a "leaky" Nod− phenotype characterized as nod- only in some trials or a delayed nodulation phenotype (Jacobs et al. (1985) J. Bacteriol. 162:469-476; and Gottfert et al. (1986) J. Mol. Biol. 191:411-420). In fact, two distinct *nod*D genes have been found in *R. fredii* USDA 191, mutants of which display distinct phenotypes (Appelbaum et al., European Publication No. 0211662 *R. fredii nod*D-rl, hereinafter designated *nod*D-2, mutants are delayed in soybean (*Glycine max* cv. Peking) nodulation and affected in exopolysaccharide synthesis, while *nod*D-r2, hereinafter designated *nod*D-1, mutants are nod− on siratro. *R. fredii nod*D-r2 has been renamed *nod*D-1 because this gene complements the *nod*D gene of *R. trifolii* that is adjacent to the *nod*ABC operon. *R. fredii nod*Dr-1 has been renamed *nod*D-2 for consistency.

It appears that *R. meliloti* strains also carry multiple *nod*D−like genes (Honna et al. (1985) in *Nitrogen Fixation Research Progress*, Evans et al. (eds.), Martinus Nijhoff Pub., Dordrecht, Netherlands, p. 120; Honna & Ausubel (1986) in *Molecular Genetics of the Plant-Microbe Interaction*, Verma et al. (eds.), Martinus Nijhoff Pub., Dordrecht, Netherlands, p. 223; Kondorosi et al. (1986) ibid., p. 217; Gottfert et al. (1986)). At least three *nod*D hybridizing regions have been located on the *R. meliloti* Sym plasmid; designated *nod*D-1 (adjacent to *nod*ABC), *nod*D−2 and *nod*D−3. *Nod*D−3 mutants appear to retain wild-type nodulation phenotype, while *nod*D−2 mutants display nodulation delays similar to *nod*D−1 mutants. Interestingly, double mutants in both *nod*D−1 and *nod*D−2 are reported to remain nod+, but display a more severe delay in nodulation. Interspecific hybridization studies using a *nod*D specific probe reported by Kondorosi et al. (1986) and Rodriguez-Quinones et al. (1987) Plant Mol. Biol. 8:61-75, also indicate the presence of two *nod*D−like genes in *R. trifolii. R. phaseolii* and a broad host range Rhizobium sp. MPIK3030.

In contrast to the fast-growing rhizobia, Sym plasmids have not been associated with nodulation by the Bradyrhizobium strains. The nitrogenase and nodulation genes of these organisms are believed to be encoded on the chromosome. Marvel et al. (1984) in *Advances in Nitrogen Fixation Research*, Veeger and Newton (ed.) Nijhoff/Junk, The Hague, Netherlands; and (1985) Proc. Natl. Acad. Sci. 82:5841-5845, have shown that a strain of *Bradyrhizobium* sp. (*Parasponia*) contains genes, associated with early nodulation, which can functionally complement mutations in *R. meliloti* gene mutants and which hybridize to the *nod*ABC genes of *R. meliloti*. The presence of *nod*D gene(s) in this strain was not reported.

Noti et al. (1985) Proc. Natl. Acad. Sci. USA 82:7379-7383 reported the isolation and characterization of nodulation genes from a strain of *Bradyrhizobium* sp. (Viona). DNA regions within a cloned segment of this strain of *Bradyrhizobium* were associated with nodulation functions using Tn5 mutagenesis and the cloned DNA was reported to complement *nod*C mutants of *R. meliloti*.

Russell et al. (1985) 164:1301-1308 report the isolation of DNA regions encoding nodulation functions in strains of *B. japonicum*. The isolated DNA region was reported to show strong homology to *nod* regions of *R. meliloti* and *R. leguminosarum*, and to functionally complement a nod-mutation in *R. fredii*. No sequence or transcript mapping of the cloned DNA was provided.

The precise biochemical role of the nod genes and their products in nodule development is unknown. Attempts to isolate nod gene mRNA and protein products from free-living Rhizobium have been unsuccessful (Kondorosi et al. 1984). Protein products of nod genes have, however, been obtained by fusion of nod genes to strong *E. coli* promoters (Schmidt et al. (1984) EMBO J. 3:1705-1711; John, M. et al. (1985) EMBO J. 4:2425-2430) or in an *E. coli* in vitro transcription/translation system (Downie et al. (1985) Mol. Gen. Genet. 198:255-262). Schmidt et al. 1984 report the expression in *E. coli* minicells of several polypeptides encoded in the *R. meliloti* common nod region. Three polypeptides of 23, 28.5 and 44 kd, respectively, were mapped to the nod gene cluster. The 44 kd protein maps to a region of DNA strongly conserved among fast-growing rhizobia. John et al., 1985 identify the 44 kd protein as the product of the *nod*C gene. A fourth polypeptide product of 17.5 kd is mapped to the region of the nod gene in *R. meliloti*. Downie et al. 1985 report the production of the presumptive nod gene products of *R. leguminosarum* by an in vitro translation/transcription system. Four polypeptides having molecular weights of 48, 45, 36 and 34 kd were reported to be the products of the nod genes. The 34 kd and 36 kd polypeptides are described as originating from a single gene and are reported to be the products of *nod*D.

The establishment of nitrogen-fixing nodules is a multistage process involving coordinated morphological changes in both bacterium and plant, so it is expected that the rhizobial nodulation genes are under precise regulatory control. It has been suggested that an exchange of signals between plant and bacterium is requisite for mutual recognition and coordination of the steps of infection and nodulation development (Nutman, P.S. (1965) in *Ecology of Soil Borne Pathogens*, eds. F.K. Baker and W.C. Snyder, University of California Press, Berkeley, pp. 231-247; Bauer, W.D. (1981) Ann. Rev. Plant Phys. 32:407-449; and Schmidt, E.E. (1979) Ann. Rev. Microbiol. 33:355-376). For example, root exudates have been linked to control of nodulation. Exudates have been reported to both stimulate (Thornton (1929) Proc. Royal Soc. B 164:481; Valera and Alexander (1965) J. Bacteriol. 89:113-139; Peters and Alexander (1966) Soil Science 102:380-387) and inhibit (Turner (1955) Annals Botany 19:149-160; and Nutman (1953) Annals Botany 17:95-126) nodulation by rhizobia.

Reports on the regulation of the nod genes of *R. meliloti* (Mulligan and Long (1985) Proc. Natl. Acad. Sci. USA 82:6609-6613) and *R. leguminosarum* (Rossen et al. (1985) EMBO J. 4:3369-3373; Shearman et al. (1986) EMBO J. 647-652) and *R. trifolii* (Innes et al. (1985) Mol. Gen. Genet. 201:426-432) have appeared. All of these studies report that *nodC* is expressed at very low levels in free-living *R. meliloti*, but is induced in the presence of plant exudate. Shearman et al. 1986 reports that in addition, *nodF* of *R. leguminosarum* is induced in the presence of plant exudates and Innes et al. 1985 reports that several other *R. trifolii* nod genes including *nodFE* and genes of region IV are induced by legume exudate. In all studies, *nodD* expression is reported to be constitutive and not to be inducible by root exudates.

In *R. meliloti* and *R. leguminosarum*, *nodD* is reported to be necessary in addition to plant factors for expression of the *nodABC* genes (Downie et al. (1985) Mol. Gen. Genet. 198:255-262; Mulligan and Long, 1985; Rossen et al., 1985). More recently, Shearman et al. (1986) EMBO J. 5:647-652, have reported that *nodD* is also required, in addition to plant factors for induction of *nodF*. Similarly, in *R. trifolii*, the *nodABC* genes are unable to confer root hair curling, that is prerequisite for nodulation, in the absence of the *nodD* gene (Schofield, Ph.D. Thesis (1984) Australian National University, Canberra). These results indicate that the *nodD* gene product has a regulatory function in fast-growing rhizobia in the expression of several other *nod* genes. The mechanism by which *nodD* regulates the expression of other *nod* genes is not fully understood, but may involve the initial interaction of *nod* directly or indirectly with legume exudate factors followed by binding of an altered *nodD* to DNA sequences in the promoter regions of the legume exudate inducible *nod* genes. The role of the multiple copies of *nodD* genes in a single strain in the regulation of nodulation is not yet fully understood.

A highly conserved nucleotide sequence has been described in the promoter regions of several legume exudate-inducible *nod* genes. This sequence precedes the *R. trifolii* *nodABC* and *nodFE* genes and the *R. meliloti* *nodABC* genes (Schofield and Watson (1986) Nucleic Acids Research 14:2891-2904). The sequence has also been identified in the promoter region of the *nodABC* genes in the slow-growing *Bradyrhizobium* sp. (*Parasponia*) Scott (1986) Nucleic Acids Res. 14:2905-2919). This sequence is believed to function in the regulation of expression of *nod* genes by chemical factors in legume exudate (Schofield et al., Innes et al., (1985 Mol. Gen. Genet. 201:426-432), possibly as a DNA binding site for nodulation regulatory proteins.

Specific components of legume exudates that act to induce nodulation gene expression in several species of Rhizobium have recently been identified. In addition, a number of compounds related in structure to the inducer components found in exudates have also been identified as inducers of Rhizobium *nod* genes.

Peters et al. (1986) Science 233:977-980 identified luteolin (3',4',5,7-tetrahydroxyflavone) as the component of alfalfa exudates that induces *nodABC* expression in *R. meliloti*. Nod gene induction was assayed as β-galactosidase expressed from a *lacZ* gene which had been fused to the *nodC* gene of *R. meliloti*. In this gene fusion, the *lacZ* structural gene was placed under the regulatory control of the *nodABC* promoter and its associated *nod*—box regulatory sequence. A number of chemical compounds structurally related to luteolin were also assayed for *nod*-gene induction in this system including several flavones, flavanones and flavanols. Of those compounds tested, only apigenin was found to induce the *R. meliloti* *nod*gene. Apigenin was found to be a much weaker inducer than luteolin.

Using similar *nod-lacZ* fusions in several *nod* genes, Redmond et al. (1986) Nature 323:632-635 reported the identification of three clover exudate components that induced expression of *R. trifolii* *nod*genes: 4',7- dihydroxyflavone (DHF), geraldone (3'-methoxy DHF) and 4'-hydroxy-7-methoxyflavone. In related work, Rolfe et al. European Publication No. 0245931, a number of substituted flavones, flavanols and flavanones were identified as *R. trifolii* *nod* gene inducers including luteolin and naringenin. Induction activity was reported to be confined to molecules having the flavone ring structure, in particular coumestrol and the isoflavones daidzein and formononetin were not active for *R. trifolii* *nod* gene induction.

Two of the nodulation gene inducers of *R. leguminosarum* from pea exudate were identified as eriodictyol (3',4',5,7-tetrahydroxyflavanone) and apigenineriodict 7-0-glucoside by Firmin et al. (1986) Nature 324:90-92. Apigenin, hersperitin and naringenin, in addition to other flavones and flavanones, were also found to be active as inducers. The isoflavones daidzein, genistein and kaempferol were reported to be antagonists which strongly inhibited the activation of *nod* genes by inducers.

Zaat et al. (1987) J. Bacteriol. 169:198-204 characterized a *R. leguminosarum* nodulation gene inducer from Vicia sativa exudate as "flavonoid in nature, most likely a flavanone." Although the exudate component was not identified, naringenin, eriodictyol, apigenin and luteolin were reported to be strong *nod*gene inducers; 7-hydroxyflavone, a somewhat weaker inducer, and chrysin and kaempferol were weak or poor inducers. Among others, the isoflavones daidzein, genistein and prunetin were reported to be inactive.

Kosslak et al. U.S. Pat. Application Ser. No. 035,516, filed Apr. 7, 1987, now abandoned, reports the identification of chemical factors which induce *B. japonicum* *nod* gene expression. The isoflavones daidzein and genistein were identified as components of soybean exudates which induced *nod*gene expression. Additionally, several other isoflavones including 7-hydroxyisoflavone, 5,7-dihydroxyisoflavone, biochanin A; formononetin and prunetin, as well as the flavone apigenin, the flavonol kaempferol and coumestrol were found to induce *nod*gene expression. These results were unexpected in that isoflavones were found not to induce *nod* gene expression in Rhizobium strains and in fact isoflavones and several other of the *Bradyrhizobium japonicum* *nod* gene inducer compounds had been reported to be antagonists of *nod* gene induction at least in *Rhizobium leguminosarum* (Firmin et al., 1986). The identification of the chemical factors which induce the nodulation genes of Bradyrhizobium sp. Parasponia has not been reported.

Recently Horvath et al. (1987) EMBO J. 6:841-848 reported a comparison of *nod*gene induction in *R. meliloti* and Rhizobium MPIK3030, a derivative of Rhizobium NGR234 which is a broad host range nodulating strain which nodulates siratro, among others. It is reported that the MPIK3030 *nodD*-1 gene induces expression of nodulation genes by interacting with plant factors from the host siratro as well as the non-host alfalfa. In contrast, *R. meliloti* *nodD* genes interact only with alfalfa exudate. *R. meliloti* transconjugates carrying the *nodD*—1 from MPIK3030 effectively nodulate siratro; however, MPIK3030 transconjugants carrying the *R. meliloti* nodD−1 do not nodulate alfalfa. A chimeric *nodD* gene having the 5' end of *nodD*−1 of MPIK3030 and the 3' end of *R. meliloti nodD*−1 was inserted into a *R. meliloti nodD*−1/*nodD*−2 mutant. The *R. meliloti* mutant transconjugant carrying the chimeric gene nodulated alfalfa normally. In contrast, an MPIK3030 mutant transconjugant carrying the chimeric gene did not nodulate siratro. These results indicate that *nodD* regulation of nodulation genes mediated by interaction with plant factors is host specific presumably by the selective interaction of *nodD* proteins with certain plant factors. The results also indicate that the carboxy end of the *nod*protein, which is the more divergent region among the *nodD* proteins, is functional in the specific plant factor interaction which can result in host specificity of nodulation. Horvath et al. note that the apparent specificity of the interaction between plant factors and *nodD* protein may result from an enhanced affinity of certain plant factors for a *nodD* protein or alternatively from a decreased susceptibility of a *nodD* to inhibiting compounds found in exudates (Firmin et al., 1986).

SUMMARY OF THE INVENTION

The present invention relates to the isolation, characterization and nucleotide sequencing of *nodD* genes of strains of *Bradyrhizobium japonicum*. These *nodD* genes function in the induction of *B. japonicum* nodulation genes in response to the application of *B. japonicum* nodulation inducing factors.

Two *nodD* genes have been identified and sequenced in *B. japonicum* strains, one located adjacent to the *nodABC* operon, designated *nodD*−1 and a second *nodD*, *nodD*−2, located downstream of the 3' end of *nodD*−1 (FIGS. 1 and 2). The relative locations of the two *nodD* genes were similar in both *B. japonicum* USDA 123 and USDA 110. Further, the nucleotide sequence of the *nodD*−1 genes of USDA 123 and USDA 110 are almost identical with a single nucleotide difference between them. The *nodD*−1 proteins differ by a single amino acid. Similarly, the *nodD*−2 genes of USDA 123 and USDA 110 appear to be identical in sequence.

The present invention provides recombinant DNA molecules which comprise *B. japonicum nodD* genes and their functional equivalents. Specifically, recombinant DNA molecules which comprise a nucleotide sequence of a *nodD* gene of a *B. japonicum* strain, particularly *nodD* genes of *B. japonicum* USDA 123 and USDA 110 are provided. *B. japonicum nodD* genes include but are not limited to *nodD*−1 and *nodD*−2 genes, specifically those of strains USDA 123 and USDA 110. In a specific embodiment, the recombinant DNA molecules pEA5-IB and pRJ103 which comprise the *nodD*−1 and *nodD*−2 genes of USDA 123 and USDA 110, respectively, are provided.

The *nodD* genes of the present invention and the DNA molecules containing them are useful for the genetic engineering of Rhizobium and Bradyrhizobium strains. These genes and DNA molecules can be used alone or in combination with other genetic constructs to enhance the competitiveness of strains for nodulation and in the selective manipulation of nodulation host range of strains.

The genes, DNA molecules and constructs containing them and the *nodD* sequence provided herein are useful in a method for the selective expression of structural genes which are placed under the control of legume exudate-inducible promoters in response to the application of *B. japonicum* nodulation gene inducing factors.

The method of the present invention generally involves the steps of (a) constructing a legume exudate-inducible expression cassette comprising a *nodD* gene of a *Bradyrhizobium japonicum* strain, a legume exudate-inducible nodulation gene promoter, and the structural gene such that the structural gene is placed under the regulatory control of the nodulation gene promoter and such that the *nodD* gene is expressed;

(b) introducing the legume exudate-inducible expression cassette into a bacterium in which the expression cassette functions; and (c) applying an amount of the nodulation inducing composition effective for inducing the nodulation gene promoter in the bacterium containing said expression cassette thereby obtaining selective expression of the structural gene.

Nodulation inducing compositions that are effective for *B. japonicum nod*gene induction comprise *B. japonicum nod*gene inducing factors, such as those described in Kosslak et al. U.S. Pat. Application Ser. No. 035,516, now abandoned filed Apr. 7, 1987, alone or in combination, present in an amount or amounts sufficient for induction of *B. japonicum* nodulation genes. Nodulation inducing compositions can comprise among others the isoflavones daidzein and genistein. Such inducing compositions can also comprise plant exudates, including legume exudates and specifically soybean exudate. Such inducing compositions can comprise fractions or extracts of such exudates. As is now known in the art, such inducing compositions must not contain inhibitory levels of those chemical factors which inhibit *Bradyrhizobium japonicum* nodulation gene induction.

Nodulation gene promoters useful in the present invention are the promoters of Rhizobium or Bradyrhizobium nodulation genes which are inducible by legume exudate and include specifically promoters of *B. japonicum* strains. Such promoters are distinguished by the presence of a conserved regulatory sequence, designated the *nod*−box. Specifically included are the *nodABC* gene promoters of both *Rhizobium* and *Bradyrhizobium* strains.

Structural genes that are useful in the present method include those genes that can be expressed in bacteria including but not limited to antibiotic resistance genes, β-galactosidase genes, and *Bacillus thuringiensis* crystal protein genes.

Bacterial strains useful in the present method include all strains in which the legume exudate-inducible expression cassette functions; preferred strains are *Rhizobium* and *Bradyrhizobium* strains, most preferred strains are *B. japonicum* strains.

BRIEF DESCRIPTION OF THE FIGURES

FIG. 3 is the DNA sequence of the *nod*D−1 of *B. japonicum* USDA 123. Both DNA strands are shown (the top line reads 5' to 3' and the bottom line reads 3' to 5'). The predicted amino acid sequence of *nod*D−1 gene product is shown below the DNA sequence. Table 1 provides the amino acid abbreviations used in FIG. 3. The position of a conserved nodulation gene regulatory sequence *nod*−box which spans a *Cla*I site preceding *nod*D is underlined. The DNA sequence of the *nod*D−1 gene coding region of *B. japonicum* USDA 110 is almost identical to that of USDA 123 with a single base change in codon 139 which is GAC in USDA 110. The deduced protein sequences of the two *nod*D−1 differ by one amino acid at position 139, which is aspartic acid (D) in USDA 110.

FIG. 4 is the DNA sequence of the *nod*D−2 gene of *B. japonicum* USDA 123. Both DNA strands are shown (the top line reading 5' to 3'). The deduced amino acid sequence of *nod*D−2 gene product is shown below the DNA sequence. Table 1 provides amino acid abbreviations used in FIG. 3. Only portions of the *B. japonicum* USDA 110 *nod*D−2 coding region have been sequenced (approximately 60%); however, in all portions sequenced the *nod*D−2 gene of USDA 110 is identical in sequence to that of USDA 123.

FIG. 5 is a comparison of the *nod*D protein coding regions of several fast- and slow-growing rhizobia, including both *nod*D−1 and *nod*D−2 sequences. The predicted amino acid sequences of the *nod*D proteins of *B. japonicum* USDA 123 (B.j.123-1 and B.j.123-2) are taken from FIGS. 3 and 4. *R. fredii* sequences (R.f.−1 and R.f.−2) are from European Publication No. 0211662. The *R. meliloti nod*D−1 and *nod*D−2 (R.m.−1 and R.m.−2) sequences are from Egelhoff et al., 1985, and Gottfert et al. (1986), respectively. *R. leguminosarum* (R.l.-1) and *R. trifolii* (R.t.−1) sequences are from Egelhoff et al., 1985, Shearman et al., 1986, and Schofield and Watson, 1986, respectively. The sequence of *nod*D of *Bradyrhizobium* sp. (*Parasponia*) (B. sp.-1) is taken from Scott (1986) Nucleic Acids Res. 14:2905-2919. The sequence of the Rhizobium sp. MPIK3030 *nod*D−1 (R. sp.-1) is taken from Horvath et al. (1987) EMBO J. 6:841-848. The sequences are aligned for best fit; a dash is used to indicate added spacing to improve overall sequence alignment. All sequences are compared with that of *B. japonicum* USDA 123 *nod*D−1 (top line of sequence). Amino acids at which sequence is conserved with *B. japonicum nod*D−1 are indicated by dots.

DETAILED DESCRIPTION OF THE INVENTION

Figure 1:
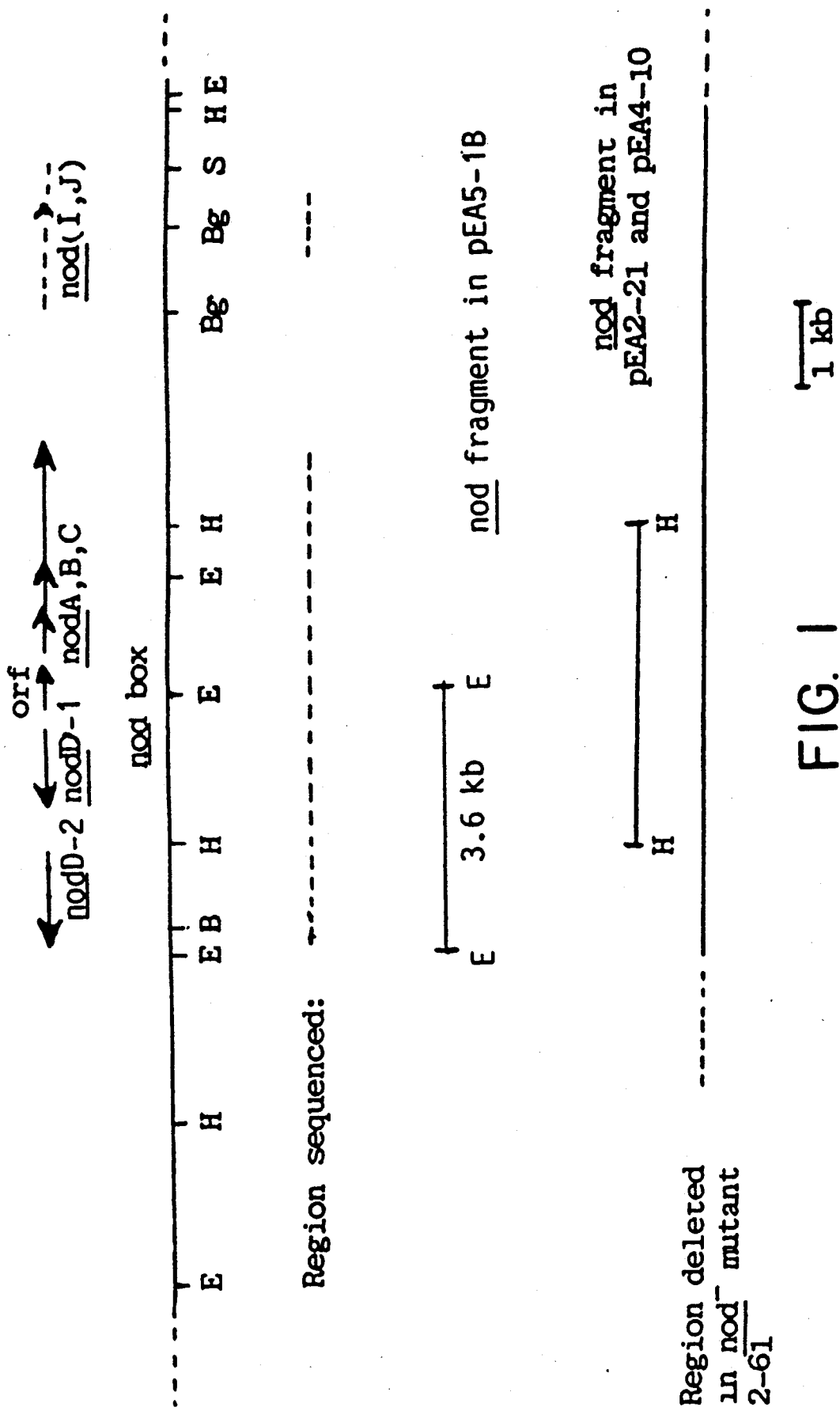
FIG. 1 is a restriction map of the *B. japonicum* USDA123 nodulation gene region. The location and orientation of the *nod*genes is indicated, including both *nodD*−1 and *nodD*−2. The DNA fragment cloned in pEA5-IB, which contains both *nodD* genes, is indicated. The region of this fragment that has been sequenced is indicated below the map. The distance between the 3' end of *nodD*−1 and the 5' end of *nodD*−2 is 638 nucleotides. The location of the conserved regulatory sequence (*nod*-box) in the *nodABC* promoter region is also indicated.

Regulatory proteins function in the regulation of expression of genes at the level of transcription. Regulatory proteins can function either in repression of gene expression (repressor), induction of gene expression (activator) or both. A single regulatory protein may be associated with the expression of several genes. Gene expression is often regulated at the transcription level with a regulatory protein controlling the initiation of transcription.

The expression of certain Rhizobium and Bradyrhizobium genes that are essential for root nodule formation, i.e. nodulation genes, is induced by chemical factors present in plant exudates, particularly legume exudates. Induction has been demonstrated to require the presence of a *nod*D gene, indicating that *nod*D proteins function in nodulation gene induction. It has also been demonstrated that certain chemical factors which may also be present in legume exudates act to inhibit nodulation gene induction. Although the mechanism of induction and the explicit roles of inducer and inhibitor molecules and the *nod*D proteins is not fully understood, it has recently been reported (Horvath, 1987) that at least in some cases the different *nod*D genes interact differently with or respond differently to the plant nodulation signal molecules (either inducers or inhibitors). Although the *nod*D proteins are recognizable as structurally related due to existence of moderate amino acid homology among these proteins, the different *nod*D genes appear to function differently in nodulation gene induction. This difference in functionality is apparently associated with the C-terminal portion of the protein which is in fact more divergent in sequence among the *nod*D proteins than the N-terminal region.

The term promoter is used in the art to designate the nucleotide sequence adjacent to the 5' end of a structural gene which is involved in the initiation of transcription. Promoters contain DNA sequence elements which insure proper binding and activation of RNA polymerase, influence where transcription will start, and affect the level of transcription. Further, specific sequences within or adjacent to promoter regions are functional in the regulation (induction or repression) of gene expression responsive to stimuli or specific chemical species. (Raibaud and Schwartz (1984) Ann. Rev. Genet. 18:173-206). The size of promoters are variable. In many cases, promoter activity is confined to approximately 200 bp of sequence in the 5'- direction from the site of transcript initiation. However, sequences out to approximately 400 bp 5' to the structural gene have been implicated in the regulation of gene expression of certain genes. The majority of promoters control initiation of transcription in one direction only, so in order to be under the control of a promoter, a structural gene must usually be located upstream (in the 3' direction) of the promoter and in the correct orientation with respect to the promoter. The distance between the promoter and the structural gene is believed to be an important factor in gene expression level. One or several genes may be under the control of a single promoter or, conversely, one or more promoters may control a single structural gene.

Comparisons of promoter sequences of a number of *E. coli* genes have revealed conserved sequence elements at −10 bp (10 nucleotides 5' to the site of initiation of transcription) and −35 bp (Rosenberg and Court (1979) Ann. Rev. Genet. 13:319–353). These sequences have been implicated in RNA polymerase binding. An average *E. coli* promoter can be represented by a consensus sequence "5'-TTGACA - - - TATAAT-3'". The distance between the two elements in this consensus sequence is also generally conserved at between 15–19 bp. Promoters having similar sequence elements have been found in other gram-negative bacteria. In contrast, eukaryotic promoters have sequence elements that are distinct from the consensus prokaryotic promoters of *E. coli*. Eukaryotic promoters are not usually functional in prokaryotes, and prokaryotic promoters are not usually functional in eukaryotes.

Environmental factors such as temperature, light and oxygen tension, and chemical species such as nutrients, metabolites, heavy metal ions and steroids have been found to regulate gene expression. Factors that induce expression as well as factors that repress expression of genes have been identified. The exact mechanisms of regulation by such signals or stimuli is likely to be complex involving multiple chemical interactions. By analogy to previous mechanistic studies of regulation, however, regulatory control of gene expression is expected to involve changing the ability of RNA polymerase to bind to DNA sequences in the promoter region. One possible mechanism is the binding of regulatory protein possibly after activation by interaction with a signal molecule to a DNA sequence at or near the position of binding of RNA polymerase to activate or prevent transcription. A second possible mechanism is direct or indirect interaction of a signal (inducer or repressor) molecule with RNA polymerase, itself, to change its specificity for recognition and binding to a DNA sequence of the promoter. In either case, specific sequence(s) within or in the vicinity of the promoter would be involved in the mechanism of regulation. Depending upon the mechanism of regulation, the presence of one or several DNA sequences could be required for regulation of gene expression.

Comparison of the DNA sequence of promoters of genes that are regulated by similar mechanisms has revealed distinct nucleotide sequences in the promoter region associated with regulation. For example, comparison of the promoters of the nitrogenase genes (nif) in *Klebsiella pneumoniae* and the fast- and slow-growing rhizobia reveals a nif promoter consensus sequence distinct from the *E. coli* consensus sequence 5'. . . YTGGCAYG . . . TTGCW . . . 3' where Y is C or T and W is A or T and in which the two sequence elements are separated by about 5 bases (Ausubel (1984) Cell 37:5–6; Better et al. (1983) Cell 85:479–485). These particular nif gene sequences may represent altered promoters responsive to positive regulation. In other cases of positive gene regulation, induction is believed to be facilitated by the presence of regulatory protein binding sites in the vicinity of the promoter.

Legume exudate inducible promoters are identifiable by the presence of a conserved regulatory sequence element designated the nod−box. This regulatory sequence element has been found in the promoter of Rhizobium nodABC and nodFE genes, among others. It is found in the *Bradyrhizobium* sp. *Parasponia* nodKABC promoter and as described herein in the intergenic promoter region between nodD−1 and nodA of *B. japonicum* strains.

Hybridization experiments using all or a portion of the nod−box conserved sequence as a hybridization probe can be employed to identify legume exudate inducible promoters. Nod−box sequences have been found in regions of the genome of *B. japonicum* strains not yet known to be associated with nodulation process, indicating that these regions contain legume exudate inducible genes which may be involved in infection or nodulation.

The conserved regulatory sequence is apparently necessary for legume exudate induction but may not be sufficient for gene expression since other promoter functions, such as ribosome binding sites, may be required. Legume-exudate inducible promoters contain, in addition to nod−box, other promoter sequences necessary for gene expression.

NodD genes are believed to be constitutively expressed in vivo, their expression being controlled by promoter sequences 5' to the start of the nodD coding region. Some nodD genes may be part of a genetic operon controlled by the promoter of the operon, for example *B. japonicum* nodD−2 expression may be controlled by the nodD−1 promoter which is found in the intergenic region between nodD−1 and ORF.

In the legume exudate inducible expression cassettes of the present invention the nodD structural genes must themselves be expressed in order to function in the expression of the structural genes that are placed under the control of legume exudate inducible nodulation promoters. The expression cassettes must contain promoter sequences which allow expression of the nodD. It would be preferable to employ the constitutive homologous nodD promoters; however, other constitutive promoters that function in the desired bacterial strain can be employed. It is also contemplated that by using methods and materials known in the art, regulatable promoters might also be employed for the expression of nodD.

Expression of a gene requires both transcription of DNA into mRNA and the subsequent translation of the mRNA into protein products. Because gene regulation usually occurs at the level of transcription, transcriptional regulation and promoter activity are often assayed by quantitation of gene products (mRNA or proteins) or by assaying for enzymatic activities of gene products. For example, promoter regulation and activity has often been quantitatively studied by the fusion of the easily assayable *E. coli* lacZ gene to heterologous promoters (Casadaban and Cohen (1980) J. Mol. Biol. 138:179–207; Okker et al., 1984; Leong et al., (1985) Nucleic Acids Res. 13:5965; Khoos and Kaiser (1984) Proc. Natl. Acad. Sci. USA 81:5816–5820; and Leglocki et al. (1984) Proc. Natl. Acad. Sci. USA 81:5806–5810). The structural gene for chloramphenicol acetyl transferase (CAT) is another gene commonly used to detect activity of promoter. Such structural genes are termed "reporter" genes, which when combined with a given promoter (usually heterologous) provide a ready assay for promoter activity.

The term homology is used in the art to describe a degree of nucleotide sequence identity between polynucleotides (RNA or DNA). Sequences that are homologous across species boundaries or between functionally similar elements are also said to be conserved. The presence of sequence homology or conservation is often used to support a genetic or functional relationship between nucleotide sequences. The degree of homology between polynucleotides is quantitatively determined as a percent homology if the sequences are known. In the absence of sequence information for comparison, the presence of homology is preferably determined operationally by hybridization experiments. A single strand of DNA or RNA will bind or hybridize to other single stranded polynucleotides whose sequences are complementary or partially complementary to their own. The strength of this binding depends on a number of factors including the degree of homology between the sequences, the nucleotide composition of the sequences, the length of the sequences and the experimental conditions used for hybridization. When hybridization is done under stringent conditions, the temperature and washing conditions of the hybridization experiment are adjusted to minimize hybridization of mismatched sequences. In the absence of sequence information, the stringency of hybridization conditions can be adjusted by the use of appropriate positive and negative controls. Recently, Rodriguez-Quinones et al. (1987) has examined the interspecific homology of the nodulation genes of Rhizobium and Bradyrhizobium strains using DNA hybridization methods and has provided experimental procedures and conditions for DNA hybridization of nodgenes.

Hybridization experiments are often used as a means of screening DNA fragments for the presence of a particular sequence or for sequences homologous to a DNA probe which is known to contain sequence(s) having a particular function. A number of alternative methods for conducting such experiments are known in the art. Hames and Higgins (eds.), 1985, provides a review of applicable hybridization techniques.

Several nodgenes, excluding nodD, have been shown to be induced by chemical factors present in legume exudates. Nodulation gene inducing factors are chemical factors like those described in Rolfe et al. U.S. Pat. application Ser. No. 844,870, filed Mar. 27, 1986, and Kosslak et al., U.S. Pat. Application Ser. No. 035,516, which are hereby incorporated by reference. Rhizobium nodulation gene inducing factors include structurally related compounds having a flavone-like ring system, for example: 7,4' dihydroxyflavone, apigenin, morin, luteolin and naringenin, among others. Bradyrhizobium nodulation gene inducing factors include both flavones and isoflavones, for example daidzein, genestein, and 7,4 -dihydroxyflavone, among others. Nodulation gene expression, as assayed by expression of lacfusions, can be induced by placing appropriate legume roots in contact with either bacterial suspensions in liquid medium or with bacterial lawns grown on agar plates. These results are consistent with the excretion by legume roots of chemical factors which induce nodgene expression. Exudates with inducing activity can be prepared by extraction of legume root or seed material. Root exudates contain a rather complex mixture of components (Hale et al. (1978) in *Interactions Between Non-Pathogenic Soil Microorqanisms and Plants* (Dommergues and Krupa, eds.) Elsevier, Amsterdam, The Netherlands, pp. 163–197), only one or several of which can be active as inducers. Components of exudate may function to inhibit the nodgene induction response. Example 4 describes the preparation of soybean exudate fractions that are active for induction of *B. japonicum* nodulation genes.

The term recombinant DNA molecule is used herein to distinguish DNA molecules in which heterologous DNA sequences have been artificially cleaved from their natural source or ligated together by the techniques of genetic engineering, for example by in vitro use of restriction enzymes or ligation using DNA ligase.

The process of cloning a DNA fragment involves excision and isolation of the DNA fragment from its natural source, insertion of the DNA fragment into a recombinant vector and incorporation of the vector into a microorganism or cell where the vector and inserted DNA fragment are replicated during proliferation of the microorganism or cell. The term cloned DNA fragment or molecule is used to designate a DNA fragment or molecule produced by the process of cloning and copies (or clones) of the DNA fragment or molecule replicated therefrom.

Except as noted hereafter, standard techniques for cloning, DNA isolation, amplification and purification, for enzymatic reactions involving DNA ligase, DNA polymerase, restriction endonucleases and the like and various separation techniques are those known and commonly employed by those skilled in the art. A number of standard techniques are described in: Maniatis et al. (1982) Molecular Cloning, Cold Spring Harbor Laboratory, Cold Spring Harbor, New York; Wu (ed.) (1979) Meth. Enzymol. 68; Wu et al. (eds.) (1983) Meth. Enzymol. 100 and 101; Grossman and Moldave (eds.) Meth. Enzymol. 65; Miller (ed.) (1972) Experiments in Molecular Genetics, Cold Spring Harbor Laboratory, Cold Spring Harbor, New York; Old and Primrose (1981) Principles of Gene Manipulation, University of California Press, Berkeley; Schleif and Wensink (1982) *Practical Methods in Molecular Biology* Glover (ed.) (1985) *DNA Cloning* Vol. I and II, IRL Press, Oxford, UK; Hames and Higgins (eds.) (1985) *Nucleic Acid Hybridization*. IRL Press, Oxford, UK; and Sellow and Hollaender (1979) *Genetic Engineering: Principles and Methods*, Vols. 1–4, Plenum Press, New York, which are incorporated by reference herein. Abbreviations, where employed, are those deemed standard in the field and commonly used in professional journals such as those cited herein.

Figure 2:
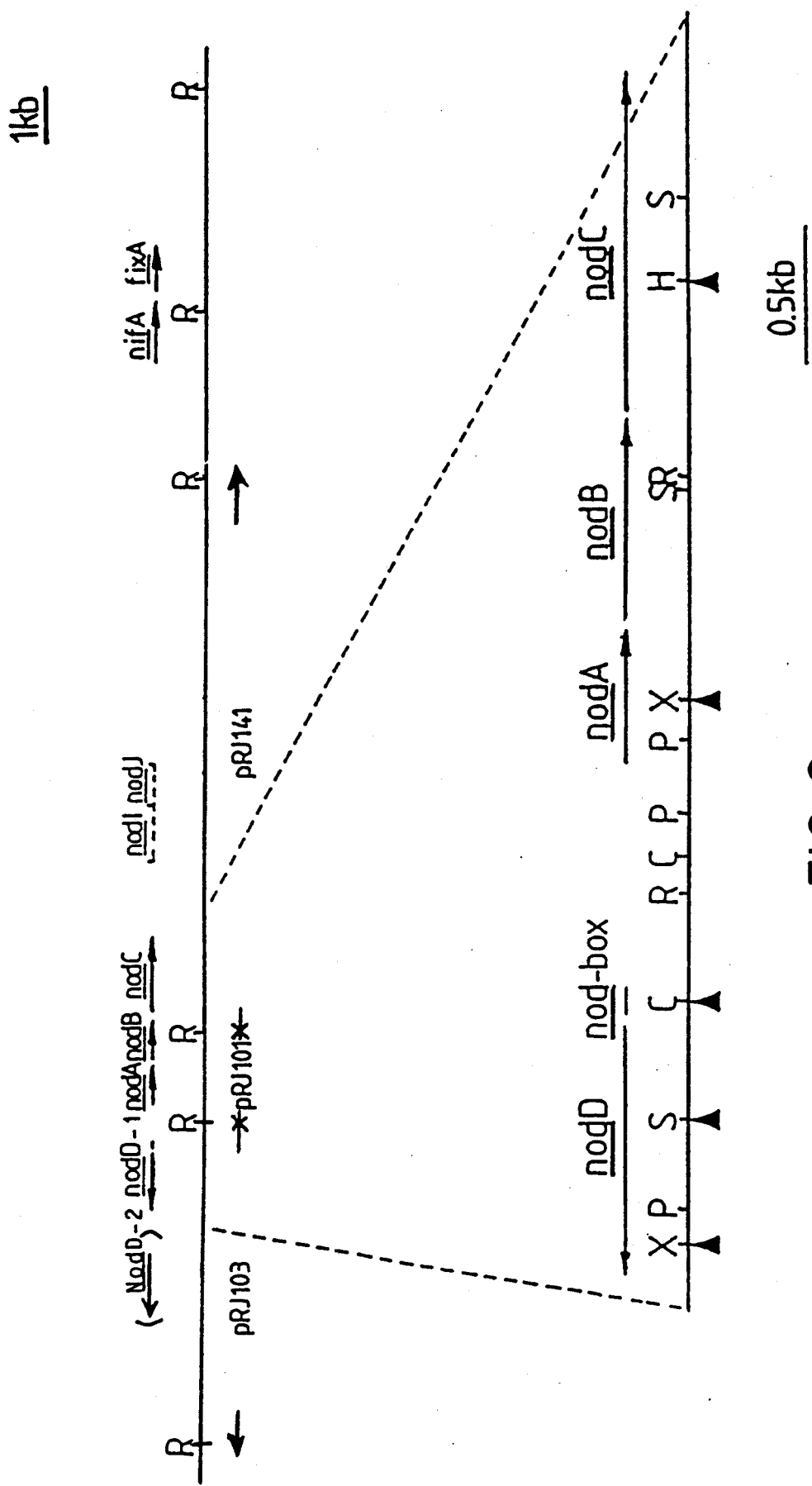
FIG. 2 is a restriction map of the *B. japonicum* USDA110 nodulation region. The *nod*ABC and *nod*D−1 gene coding regions are shown, with arrows indicating the direction of gene transcription. The *nod*D−2 coding region of USDA110 is located similarly with respect to the USDA110 *nod*D−1 as the *nod*D−2 gene in USDA123 is located to the USDA123 *nod*D−1. The approximate location of USDA110 *nod*D−2 is indicated. In this figure C=*Cla*I, H=*Hin*dIII, P=*Pst*I, R=*Eco*RI, S=*Sal*I and X=*Xho*I. The designations of plasmids containing particular *Eco*RI fragments are given beneath the map. *Eco*RI fragment pRJ103 contains both the *nod*D−1 and *nod*D−2 gene sequences. An expanded scale map of the nodulation region is also shown. The location of the iteration of the regulatory sequence in the *nod*D-*nod*A intergenic region is indicated as *nod*−box.

DNA regions from the genome of both *B. japonicum* strains USDA 123 and 110 which are homologous to nod gene probes from fast-growing rhizobia have been isolated using DNA hybridization experiments. Restriction enzyme analysis of the nod gene regions of *B. japonicum* USDA123 (FIG. 1) indicate that one nodD gene is closely linked to the nodAB genes and that this nodD is read divergently from nodAB. In similar hybridization experiments, nod gene regions from the genome of *B. japonicum* USDA110, homologous to *R. phaseolus* and *R. leguminosarum* nod gene probes were isolated. One region of *B. japonicum* 110 DNA which contained sequences that hybridized to nodB and nodC gene probes was studied in detail and the nod gene homologous sequences were mapped by restriction endonuclease analysis. FIG. 2 shows the location and organization of the nodABC and D genes in *B. japonicum* strain USDA110. Again, one nodD gene is closely linked to an apparent nodABC operon, and read divergently from the operon.

A second nodD—like gene was detected downstream (3' to) nodD—1 in the USDA123 nod region by hybridization using a nodD—2 gene of *R. fredii* probe. The nodD—2 is separated from nodD—1 by 638 bp of sequence and is transcribed in the same direction as nodD—1. It has not yet been determined if the intergenic region between nodD—1 and nodD—2 contains another open reading frame and/or promoter sequences for expression of nodD—2. It is therefore not yet clear whether nodD−2 is coordinately transcribed with nodD−1.

In fast-growing rhizobia and Bradyrhizobium sp. (Parasponia) a highly conserved regulatory sequence, the "nod−box", has been found upstream from the nodA gene. The presence of this sequence has not been previously demonstrated in B. japonicum strains. A 22-mer oligonucleotide mixed probe was synthesized based on the consensus regulatory sequence derived from fast-growing rhizobia (5'-ATCSAAACAATCRATTT-TACCA-3'; where S=G or C and R=G or A). This probe was radioactively end-labelled and hybridized to the DNA digests from the cloned nodulation region of B. japonicum USDA110 and B. japonicum total DNA. With total DNA, six hybridizing bands (2 strongly hybridizing, 4 weakly hybridizing bands) were detected. One of the strongly hybridizing fragments corresponded to the region between the fragments nodA and nodD genes. The detection of several copies of the regulatory sequence in hybridization studies suggests the presence of other legume exudate inducible genes in the B. japonicum genome in addition to nodABC.

Both B. japonicum USDA123 nodD genes have been localized to a single 3.6 kb EcoRI fragment of genomic DNA cloned in the fragment designated pEA5-lB. The locations of the nodD coding regions within pEA5-lB are shown in FIG. 1. The entire coding region of both the nodD−1 gene and the nodD−2 gene in this fragment have been sequenced. FIG. 3 provides the sequence of nodD−1 as well as 120 bp of upstream sequence including the nod−box. The predicted amino acid sequence of the nodD−1 product is also given in FIG. 2. Sequencing results for strain USDA123 confirm the presence of a conserved nodulation gene regulatory sequence adjacent to the nodD coding region (underlined in FIG. 1). FIG. 4 provides the sequence of B. japonicum USDA123 nodD−2 along with the predicted amino acid sequence of the nodD−2 product.

In B. japonicum USDA110, both nodD−1 and nodD−2 have been localized to an EcoRI fragment cloned in a plasmid designated pRJ103. This fragment was used for nucleotide sequencing.

The nodD−1 gene of USDA110 has been completely sequenced and found to be almost identical to that of nodD−1 of USDA123. There is a single nucleotide difference at codon 139 which is GAC in USDA110. This difference in DNA sequence leads to a change in amino acid sequence at this position to aspartic acid in the USDA110 nodD−1 product. The nodD−2 gene of USDA110 is located with respect to USDA110 nodD−1 similarly to the relative locations of nod−D1 and nodD−2 in USDA123. Portions of the USDA nodD−2, representing approximately 60% of the coding region, have been sequenced. In all regions thus far sequenced the USDA 110 nodD−2 sequence is identical to that of the USDA123 nodD−2.

In order to confirm that the B. japonicum USDA110 cloned regions (FIG. 2) carried nodulation genes, specific mutants were prepared by insertion of fragments of the transposon Tn5 (carrying kanamycin resistance) into several nod gene homologous regions. Insertion mutants were made in vitro at specific endonuclease restriction sites within the cloned nod gene coding regions. The mutated regions were then mobilized, by conjugation into B. japonicum USDA110 and selection was made for marker exchange into the homologous gene on the genome. Mutants having insertions disrupting the nodD−1 gene display a delayed nodulation phenotype compared to the wild-type. Similar mutations in nodD−2 gene display an apparent wild-type nodulation phenotype. Mutants having double mutations in both nodD−1 and nodD−2 display a more pronounced nodulation delay than the nodD−1 mutants; however, they remain nod+. This result suggests that at least one other nodD-like gene may be present in the B. japonicum genome.

A comparison of the nodD regulatory protein sequences of fast-and slow-growing rhizobia is presented in FIG. 5. It should be noted that in most cases herein the term nodD−1 is used to designate a nodD gene located adjacent to a nodABC operon, with the term nodD−2 used to designate a second nodD gene in a particular strain. In R. fredii, neither of the nodD genes has been linked with nodABC genes. In this case, the R. fredii nodD gene previously designated nodD-r2 which functionally complements the R. trifolii nodD−1 gene is herein designated nodD−1. R. fredii nodD-rl is herein designated nodD−2.

A significant region of nodD protein sequence near the ( N-terminal (approximately the first 80-90 amino acids, representing about 25% of the sequence) of the protein is structurally conserved in all strains of Bradyrhizobium and Rhizobium for which nodD sequence data are available. In contrast, the remaining approximately 75% of the nodD protein sequence toward the C-terminal is less conserved. Regions of the nodD proteins that are structural conserved are expected to be associated with conserved function among nodD genes, while less conserved regions are expected to be associated with functional differences between the nodD genes. In particular, the C-terminal portion of nodD proteins at least in some cases appears to be associated with differential interaction of nodD genes with nodulation inducing factors or nodulation inhibitors. Such differential interactions are believed to effect host specificity of nodulation.

Certain nodD proteins may have distinguishing regulatory functions other than selectivity of interaction with plant signal. NodD proteins may in some cases effect the level of expression of nodulation genes possibly in coordination with another nodD. Alternatively, different nodD proteins may regulate expression of different genes involved in infection or nodulation.

The relative homologies of pairs of nodD proteins can be readily ascertained by examination of FIG. 5. B. japonicum nodD−1 and nodD−2 proteins are only about 65% homologous with almost complete sequences divergence near 10 the C-terminus. This suggests that the two nodD proteins in B. japonicum have different functions in nodulation gene regulation. The two B. japonicum nodD proteins are not significantly more homologous to one another than they are to nodD proteins of Rhizobium strains. The two nodD proteins of R. fredii are also only about 68% homologous. In contrast, the two nodD proteins of R. meliloti are about 86% homologous.

The B. japonicum nodD−1 protein was found to be strikingly homologous to the nodD−1 protein of (Bradyrhizobium sp. Parasponia). The two nodD proteins are about 91% homologous over the first 314 amino acids of the protein sequence. However, the Bradyrhizobium sp. Parasponia nodD has 24 more amino acids at the C-terminus than the B. japonicum nodD−1 protein. The high conservation of amino acid sequence between these two nodD proteins from different species of Bradyrhizobium is unexpected based on the lower, although significant, homologies observed between nodD proteins of different species of Rhizobium. While the two species of Bradyrhizobium do have overlapping host ranges, since strains of both species nodulate siratro and cowpea, there is no experimental evidence that these proteins function in the same way. It is not clear what the role of the Bradyrhizobium sp. Parasponia) nodD−1 gene is in induction on siratro, as mutation of this gene results in a wild-type nodulation phenotype on siratro. The nodD−1 gene of B. japonicum does function in soybean nodulation and Bradyrhizobium sp. Parasponia apparently do not nodulate soybean. It would therefore seem that these Bradyrhizobium nodD−1 proteins do not have a common function. It is not known how much sequence homology between nodD proteins is required for functional equivalence. Furthermore, since the C-terminal region of the nodD proteins has been associated with differential function of the proteins, one might expect from the structural difference at the C-terminus that the function of these two proteins was quite different.

For the purposes of the present invention, functional equivalents of the B. japonicum nodD proteins are proteins which induce expression of B. japonicum nodulation genes in response to application of certain nodulation inducing factors such as those effective for B. japonicum nodulation gene induction, which were identified by Kosslak et al., U.S. Pat. Application Ser. No. 035,516, filed Apr. 7, 1987, which is incorporated herein by reference. Functional equivalents of the B. japonicum nodD genes are genes which encode proteins which are functionally equivalent to the B. japonicum nodD proteins. The ability of a nodD protein to induce expression of b. japonicum 286 nodulation genes in response to application of nodulation gene inducing factors can be readily ascertained without undue experimentation using, for example, the nod−lacZ fusion gene expression assay that is described herein in Examples 2 and 3, and the use of which is exemplified in Examples 4 and 5.

Construction of Recombinant Vectors for Leoume Exudate-Inducible Expression of Cloned Foreign Structural Genes Once the legume exudate inducible promoter regions of the nodulation genes have been isolated, sequenced and cloned, it is possible to delete the nodulation structural genes (DNA normally transcribed under the control of these promoters) and replace them with a structural gene isolated from an extraneous source. This heterologous structural gene is thus placed under the control of the nodulation gene promoters and can be expressed under conditions where the nodulation gene promoters are active. The legume exudate inducible promoter/foreign structural gene combination or chimeric gene can then be inserted into a vector, followed by introduction of the vector into a strain of bacterium in which the nodulation gene promoter is active. Alternatively, the composite gene or chimeric gene which includes the heterologous structural gene and the legume exudate-inducible promoter can be integrated into the chromosome of the host bacterium in order to maximize the stability of the trait conferred by the chimeric gene. The nodulation gene promoters are likely to be active (induce expression responsive to legume exudate) in strains of Rhizobium, Bradyrhizobium, and possibly the taxonomically related Agrobacterium.

The foreign structural gene must be inserted in the correct position and orientation with respect to the promoter in order to obtain expression of the structural gene controlled by the promoter. The foreign structural gene must be inserted downstream of the promoter. A second aspect of correct positioning of the structural gene refers to the distance, in base pairs, between the functional elements of the promoter and the translation start site of the foreign structural gene. Substantial variation appears to exist between promoters with respect to this distance. Therefore the structural requirements in this regard are best described in functional terms. Optimal spacing can be achieved by experiments varying the length of this distance. As a first approximation, reasonable operability can be obtained when the distance between the promoter and the inserted foreign gene is similar to the distance between the promoter and the gene that it normally controls.

An alternate construction that will lead to a fusion protein is the insertion of a heterologous structural gene into an existing nodulation gene, analogous to insertion of MudI17 transposon into nod genes as described in Innes et al (1985) supra. The construction of B. japonicum nodC−lacZ fusions in Example 2 represents a specific example of the insertion of a heterologous structural gene into a legume exudate-inducible nodulation gene, thereby placing the structural gene under the control of a legume exudate-inducible promoter. An additional positioning requirement in the case of fusion protein constructions is that the structural gene must be inserted such that the coding sequence of the two genes are in the same reading frame (or in phase), a structural requirement that is well understood in the art.

Another alternative construction for expression of foreign structural genes under the control of the nodulation promoters is an expression cassette. An expression cassette can be constructed, for example, by the removal of the appropriate regulatory regions from the rhizobial DNA, followed by their insertion into a vector to form a recombinant vector. This recombinant vector would be constructed such that a unique cloning site would be positioned downstream from the nodulation gene promoter. Foreign structural genes could then be inserted into this unique cloning site and thereby placed under the control of the nodulation gene promoter. Such an expression cassette would contain a complete nodD coding region, as well as the nodD−nodA intergenic region, which contains both the nodD promoter and the legume exudate inducible nodA promoter.

The novel DNA constructions, vectors and plasmids disclosed herein are useful for amplifying the quantity of foreign structural genes, for transferring such foreign genes to selected host bacterial strains, for generating new bacterial strains and as intermediates for the construction of vectors having one or more of the foregoing uses. Bacterial strains containing the novel constructions described herein are useful for expressing foreign structural genes under certain specific conditions (on contact with legume exudate). Examples of proteins that can be usefully expressed under such conditions include insect toxin 10 protein of Bacillus thuringiensis, hydrogenase (found in some, but not all, rhizobial strains), metallothionine and prolactin. The foregoing list is not intended as limiting but merely as exemplary of the broad range of possibilities for selective synthesis of proteins on contact with plant exudate or nodulation gene inducing factors. In general, the invention makes it possible to produce any protein that may be of use either as a product extracted from culture or produced in situ in the vicinity of plant roots. The protein could confer an advantage for the host plant or for the bacterium in contact with the plant.

The following examples are intended to illustrate the invention only and are not intended to limit the scope of the invention.

EXAMPLE 1

Cloning and DNA Sequence Analysis of the nodD Gene Region of Bradyrhizobium USDA123

*B. japonicum* USDA123 was obtained from D. Weber and H. Keyser, U.S. Department of Agriculture, Beltsville, Md. *B. japonicum* USDA123 Spc is a spontaneous mutant of USDA123 that is resistant to 1000 μg/ml spectinomycin. This strain was isolated by T. McLoughlin and is on deposit with Agrigenetics Advanced Sciences Company, 5649 East Buckeye Road, Madison, Wis. 53716.

Total genomic DNA of USDA123 was purified (Scott et al. (1981) *J. Mol. Appl. Genet.* 1:71-81), digested to completion with the restriction enzyme EcoRI, fractionated by agarose gel electrophoresis, transferred to nitrocellulose, and hybridized with radioactive probes using standard procedures as described by Maniatis et al., 1982, and reviewed in Hames and Higgins, 1985. A probe containing a 3.0 kb fragment of *R. fredii* USDA191 that contained a nodD gene Appelbaum et al. (1985) *Nitrogen Fixation Research Progress*, Evans et al. (eds.), Martinus-Nijhoff, p. 101-107) hybridized strongly to a 3.6 kb EcoRI fragment of USDA123. Probe pRmSL42, which contains nodA, nodB, and the amino terminal ends of nodD and nodC of *R. meliloti* (Egelhoff et al., 1985) hybridized to a 3.6 kb fragment and to a 1.6 kb fragment of USDA123. The vector portions of these probes did not hybridize to the USDA123 fragments. This preliminary analysis suggested that USDA123 contained a nodD—homologous gene on a 3.6 kb EcoRI fragment and other nod sequences on a 1.6 kb EcoRI fragment.

Two *B. japonicum* gene banks (Bank A and Bank B) were prepared. Bank A was prepared from USDA123 soc EcoRI fragments in a phage vector using standard techniques (Maniatis, 1982). Total genomic DNA was purified (Scott, 1981) and digested to completion with EcoRI restriction enzyme. DNA was prepared from the vector Charon 3 (Blattner et al. (1977) *Science* 196:161-169) and digested with EcoRI and XbaI. XbaI was included in order to cleave the central EcoRI vector fragment and reduce reinsertion of this fragment into the vector. The digested USDA123 spc and Charon 3 DNA was ligated together and packaged into phage heads using conventional techniques. This can be readily accomplished using a commercially available packaging extract, for example Packagene (Trademark, Promega Biotech, Madison, Wis.). The packaging reaction resulted in $1.5_7 \times 10^5$ plaque forming units (titred on *E. coli* strain K802 (Maniatis, 1982)). DNA restriction analysis of several potential recombinant phage indicated that about 10% of the phage contained inserts of one or more *B. japonicum* DNA fragments. The remaining phage contained no inserts or reinsertion of the phage EcoRI fragment This library was amplified by propagating $5 \times 10^4$ phage in *E. coli* K802 to yield a mixture of $1.3 \times 10^{10}$ phage. This amplified bank is designated Bank A.

Bank B was prepared from partially EcoRI digested USDA123 DNA in a broad host range cosmid vector using conventional procedure (Maniatis, 1982). Again total genomic DNA was prepared as in Scott, 1981, and partially digested with EcoRI. The partially digested DNA was then fractionated on a sucrose gradient. Fractions containing DNA ranging in size from 12-50 kb were pooled. The vector pLAFR1 (Freedman et al. (1982) *Gene* 18:289-296) was digested to completion with EcoRI, ligated to the pooled USDA123 DNA fractions, and packaged as described above for Bank A. The package cosmids were then introduced into *E. coli* strain HB101 (Maniatis et al., 1982). Restriction analysis of several cosmids from two packaging reactions showed that all of the tested cosmids from the first reaction contained *B. japonicum* DNA inserts; while only 65% of the cosmids from the second reaction contained *B. japonicum* DNA inserts. A total of 6200 cosmids were saved and used for screening. These cosmids constitute Bank B.

The phage bank (Bank A) was screened using standard procedures (Maniatis et al., 1982) for plaques capable of hybridizing to a 3.0 kb EcoRI fragment that contains a nodD gene from fast-growing *R. fredii* strain USDA191. This 3.0 kb fragment contained the nodD gene now designated nodD—1 which complements the nodD gene of *R. trifolii*. In this screening, the 3.0 kb fragment was contained in a plasmid that consisted of the pSUP202 vector (Simon et al. (1983) *Molecular Genetics of the Bacteria-Plant Interaction*, Puhler (ed.), Springer-Verlag), the 3.0 kb EcoRI fragment (cloned into the unique EcoRI site of pSUP202), and a fragment containing the kanamycin resistance gene of transposon Tn5 cloned into the unique BamHI site of the 3.0 kb fragment (Appelbaum et al., 1985). This composite plasmid was labeled by nick translation and used as a probe to screen Bank A. Nitrocellulose filters containing 150,000 plaques from Bank A were hybridized to the probe. Several strongly hybridizing plaques were identified. One such plaque was picked, repurified (in strain *E. coli* K802), and used for preparation of phage DNA. EcoRI restriction analysis of phage DNA revealed the presence of a fragment 3.6 kb in size which hybridized to the Rhizobium nodD probe when analyzed by Southern blot analysis. This fragment was subcloned in vector pUC19 (Norrender et al. (1983) *Gene* 26:101-106) and used for DNA sequencing. This subclone is designated pEA5-1B.

The cosmid bank was screened using standard procedures (Maniatis, 1982) for cosmids capable of hybridizing to the 2 kb BamHI/HindIII fragment of pRmSL42 that contains nodDABC sequences of *R. meliloti*. The 2 kb fragment was purified by agarose gel electrophoresis after digestion of pRmSL42 with BamHI and HindIII. This fragment was labeled by nick translation and used as a probe to screen Bank B. Nitrocellulose filters containing 1000 HB101 colonies with cosmids (700 from packaging reaction no. 1 and 3000 from reaction no. 2) were hybridized to the probe. One strongly hybridizing cosmid was found. This cosmid contained a 1.6 kb EcoRI fragment that was subsequently shown by DNA sequencing to contain nodAB sequences. The cosmid did not contain any EcoRI fragments hybridizing to the nodD sequences in the probe. The 1.6 kb EcoRI fragment was subcloned in pUC19 (Norrender et al., 1983), purified (after digestion of the subclone with EcoRI), and used as a probe to screen approximately 5000 more cosmids from Bank B. Five strongly hybridizing colonies were identified. One such cosmid, designated pEA71-1A, was picked, repurified, and used for preparation of cosmid DNA. *Eco*RI restriction analysis of this approximately 30 kb cosmid insert revealed the presence of several *Eco*RI fragments, including a second 1.6 kb fragment which hybridized to the 1.6 kb *nod*AB probe described above and a 3.6 kb fragment which hybridized to the 3.6 kb *nod*D fragment of pEA5-1B. Southern blot analysis of this cosmid insert using several restriction enzymes strongly suggests that the 3.6 kb *nod*D fragment and 1.6 kb *nod*AB fragment are adjacent to each other in this cosmid.

A restriction map of the 3.6 kb *Eco*RI fragment pEA5-1B which contains *nod*D hybridizing regions was deduced by analysis of DNA fragments produced by digestion of pEA5-1B and a second plasmid which contained the *nod*D insert in the reverse orientation. The restriction map of the *B. japonicum* nodulation region, which includes the 3.6 kb pEA51-B fragment is shown in FIG. 1. A portion of the fragment has been sequenced (Maxam and Gilbert (1977) Proc. Natl. Acad. Sci. USA 74:560) as indicated in FIG. 1. The sequence of *nod*D−1, adjacent to the *nod*ABC genes is presented in FIG. 3.

The DNA sequence was scanned for homology with *nod*D genes from *R. meliloti* (Egelhoff et al., 1985), *R. trifolii* (Schofield and Watson, 1986), Bradyrhizobium sp. (Parasponia) strain ANU289 (Scott, (1986)Nucleic Acids Res. 14:2905-2919 and the *nod*D−like gene of *R. fredii* USDA191 that is carried on a 3.0 kb *Eco*RI fragment European Publication No. 0211662. An open reading frame (ORF) containing a *nod*D-homologous sequence was found. This ORF is *nod*D−1.

The sequence was examined for the presence of a conserved regulatory sequence that has been identified in both fast- and slow-growing rhizobia. An iteration of the regulatory sequence was found as indicated in FIG. 1, in the region which presumably contains the promoter of the *nod*ABC operon.

Restriction analysis of the cosmid from Bank B that contains both *nod*D and *nod*AB pEA71-1A, together with DNA sequence analysis of *nod*D and *nod*AB, indicates that *nod*D−1 is located approximately 800 bp away from *nod*AB, that the direction of translation of the *nod*D open reading frame is divergent from the *nod*A and *nod*B open reading frames, and that the regulatory sequence is located between *nod*D−1 and *nod*AB. Thus, the organization of *nod*D−1, and *nod*AB genes is very similar to that reported for both fast- and slow-growing rhizobia. This, in addition to the presence of the regulatory sequence homologous to those in fast-growing strains indicates that the regulation of at least the *nod*AB genes is similar in both fast- and slow-growing rhizobia.

Hybridization experiments in which subfragments of the 3.6 kb *Eco*RI *nod* gene fragment were probed using a *R. fredii* USDA 191 fragment specific for *nod*D−2 indicated the presence of a second *nod*D homologous region downstream of the first *nod*D gene. The presence of this *nod*D−2 gene was confirmed by sequence analysis. The DNA sequence of *nod*D−2 and deduced amino acid sequence of its protein product are presented in FIG. 4. The presence of a *nod*D−2 gene in *B. japonicum* USDA 110 was confirmed by DNA sequence analysis of the corresponding region in pRJ103.

The plasmids pEA5-1B and pRJ103 containing both the *nod*D genes of *B. japonicum* USDA 123 and USDA 110, respectively, have been introduced into *E. coli* strain JM83 (Vieira and Messing (1982) Gene 19:259-268) and have been placed on deposit with the Northern Regional Research Laboratory, 1815 North University Street, Peoria, Ill. 1604, JM83 (pEA5-1B) having Accession No. B-18077 and JM83 (pRj103) having Accession No. B-18076.

EXAMPLE 2 Construction of *B. japonicum* nodC-lacZ fusions

Clones and subclones containing the *nod* region of *B. japonicum* USDA 123 were obtained as described above in Example 1.

Figure 6:
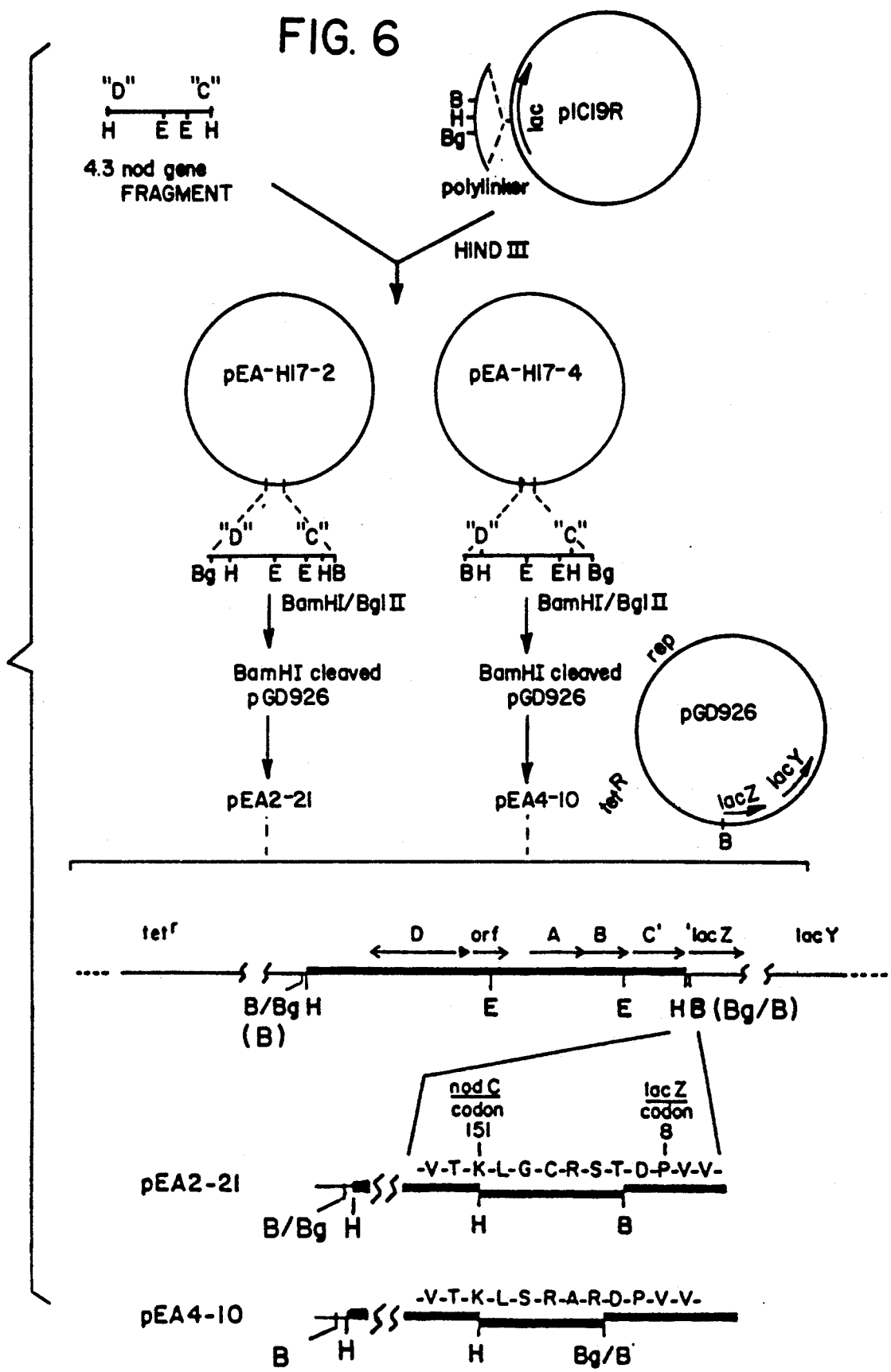
FIG. 6 is a schematic diagram of the construction of plasmids pEA2-21 and pEA4-10 which was taken from Kosslak et al., U.S. Application Ser. No. 035,516, now abandoned filed Apr. 7, 1987.

A 4.3 kb *Hind*III fragment of the *nod* region of USDA 123 (indicated in FIG. 1) which contained *nod*D, the promoter regions of *nod*D and *nod*A, including *nod*−box , *nod*A, *nod*B and the amino terminal end of *nod*C was subcloned into the unique *Hind*III site of the vector pIC19R (Marsh et al. (1984) Gene 32:481-485). In this vector, the *Hind*III site is flanked by a unique *Bam*HI site on one side and a *Bgl*II site on the other side. Clones containing both orientations of the insert were obtained (see FIG. 6). In clone pEA-H17-4, the insert is flanked by a unique *Bam*HI site on the *nod*D side of the insert and a *Bgl*II site on the *nod*C side of the insert. Clone pEA-H17-2 contains the insert in the opposite orientation, with a *Bgl*II site on the *nod*D side of the insert and *Bam*HI site on the *nod*C side.

pEA-H17-4 and pEA-H17-2 were each digested with *Bam*HI and *Bgl*II restriction endonucleases, and the resulting 4.3 kb fragments containing the *nod* genes were cloned into *Bam*HI digested pGD926 (Ditta et al (1985) Plasmid 13:149-153). The 4.3 fragment from pEA-H17-2 yielded a clone pEA2-21 in which *nod*C is joined in frame to *lac*Z by a *Hind*III-*Bam*HI linker sequence which encodes 7 amino acids. The fragment from pEA-H17-4 yielded a clone, pEA4-10 in which *nod*C is joined in frame to *lac*Z by a *Hind*III-*Bol*II/-*Bam*HI linker sequence that encodes 6 new amino acids.

Plasmids pEA2-21 and pEA4-10 behaved identically in all *nod/lac*Z expression assays preformed. Each construction has certain advantages for further genetic manipulations. The unique *Bam*HI site in the *nod*C-−*lac*Z intergenic linker in pEA2-21 is a useful site for the insertion of other genes in order to place them under the control of the *nod*A promoter. The unique *Bam*HI site downstream of *nod*D in pEA4-10 is a useful site for insertion of the second *nod*D gene of *B. japonicum* and can also be used for insertion of heterologous genes in order to place them under the control of the *nod*D promoter.

Plasmids pEA2-21 and pEA4-10 were routinely propagated in *E. coli* MC1061. The plasmids were mobilized into *B. japonicum* by standard crosses in which a helper plasmid, pRK2013 (Ditta et al. (1980) Proc. Natl. Acad. Sci. USA 77:7347-7351) provides transfer functions. Each mating consisted of a mixture of three strains: the donor strain, *E. coli* MC1061 containing either pEA2-21 or pEA4-10, the helper strain, *E. coli* K802 containing pRK2013, and the Bradyrhizobium recipient strain. Spontaneous spectinomycin (spc) resistant mutants of the various Bradyrhizobium strains were used as recipient strains. Both *nod*−*lac* fusion plasmids also carry tetracycline resistance. The mating mixtures were incubated in non-selective media to allow mating to occur after which they were plated on selective media containing tetracycline (75mg/1) and spectinomycin (250 mg/1). Colonies that grow on the selective media should be transconjugant Bradyrhizobium strains which carry the *nod*−*lac* fusion plasmid. Transconjugants were selected, repurified and then typed by standard serological techniques using strain-specific antisera that distinguish the rhizobia from each other and from *E. coli*.

Induction of expression of the USDA123 nodC—lacZ fusions was examined in the *B. japonicum* strains USDA123 spc and USDA110 spc which are spontaneous spc resistant mutants of the wild-type strains. *Bradyrhizobium japonicum* USDA123 spc containing pEA2-21 and *B. japonicum* EA2-61 (nod—deletion mutant) containing pEA2-21 have been placed on deposit with the Northern Regional Research Laboratory (NRRL), 1815 North University Street, Peoria, Ill. 61604, and given the accession numbers B-18193 and B-18192, respectively.

EXAMPLE 3

Assay for Induction of *B. japonicum* nod Genes

Exponentially growing cultures of strains containing pEA2-21 or pEA4-10 were incubated with soybean root exudate preparations or fractions, see Table 2, or with ethanol solutions of flavones, isoflavones and related compounds, see Table 3. In the case of addition of ethanol solutions of individual compounds, the final concentration of ethanol in the culture was always less than 2% (v/v) and an equivalent amount of ethanol was included with controls. Samples and controls were incubated at 28° C., after which aliquots were taken for $\mu$-galactosidase assay and measurement of culture turbidity (O.D. 600).

The standard o-nitrophenyl-$\beta$-D-galactoside (ONPG) $\beta$-galactosidase assay of Miller (1972) *Experiments in Molecular Genetics*, Cold Spring Harbor Press, Cold Spring Harbor, N.Y. was used. Samples were treated with toluene to permeabilize cells, incubated with ONPG for up to two hours after which the absorbance of the sample at 420 nm was measured. $\beta$-galactosidase activity is expressed in "Miller units" (U) which are defined by the equation:

$$U = 1000 \times O.D.420 / V \times T \times O.D. 600$$

where O.D. 420 is the absorbance at 420 nm, O.D. 600 is the absorbance at 600 nm (culture turbidity), V is the volume of culture mixed with buffer (total sample volume is 1 ml) and T is the time of incubation with ONPG in minutes.

EXAMPLE 4

Identification of soybean exudate components that induce nod—lac fusions in strains of *Bradyrhizobium japonicum*

Seeds of *Glycine max* cv. Williams were surface sterilized for 10 minutes in commercial bleach, rinsed once with sterile distilled water, immersed for 5 minutes in 1% (v/v) HCl and finally rinsed six times with sterile distilled water. Sterilized seeds were germinated by culturing on 1% (wt/v) yeast extract-mannitol agar for three days at 27. C. For preparation of plant exudate, 200 g of seeds were germinated. Three day old seedlings were extracted for 24 hr. in 300 ml of a 9:1 (v/v) mixture of methanol/water followed by a second extraction (24 hr) in 300 ml of a 1:1 (v/v) methanol/water mixture. The methanolic extracts were combined and the solvent was removed under vacuum. The resulting residue (7.8 g) was dissolved in water (200 ml) and the solution was filter sterilized using a 0.22 micron cellulose acetate filter. This material is whole soybean exudate and is designated fraction I.

A portion (150 ml) of fraction I was extracted (3x) with anhydrous ethyl ether and dried. The ether extract was concentrated to dryness under vacuum. The resulting residue (40 mg) was dissolved in 100ml of a 1:99 (v/v) ethanol:water solution, filter sterilized and the pH was adjusted to 6.5 for biological assays. This ether soluble fraction was designated fraction II.

The remaining water-soluble fraction (ether extracted fraction I) was concentrated to dryness under vacuum and the residue (6.16 g) was dissolved in 150 ml of water and the resulting aqueous solution was filter sterilized. This fraction was designated fraction III.

A portion of fraction III (73 ml) was hydrolyzed in acid (6% v/v concentrated HCl) for 1 hr at reflux. The resultant hydrolysate was extracted with ether (5×). The ether extract of the hydrolysate was concentrated to dryness under vacuum and the resultant residue (100 mg) was dissolved in HPLC grade methanol. This material was designated fraction V. For use in bioassays, methanol was removed under vacuum from 1 ml aliquots of fraction V and the residue was then dissolved in 1 ml of punctilious ethanol.

The water-soluble, ether extracted hydrolysate, was concentrated to dryness under vacuum, the residue was dissolved in water, the pH adjusted to 6.5 and the solution was filter sterilized. This material was designated fraction IV.

Fractions I–V were assayed as described in Example 3 for nod gene induction activity in both *B. japonicum* USDA 110 and 123. In addition, 10, 100 and in most cases 1000 fold dilutions of each fraction were assayed. The results of these assays are shown in Table 2. All fractions displayed nod gene inducing activity; however, when induction as measured in Units of $\beta$-galactosidase activity was adjusted for the concentration of the fraction (mg residue/ml), two fractions, II and V, display much higher inducing activity/mg residue. Fraction II and Fraction V were found to be from 1000 to 10,000 times more active on a weight basis than any of the other fractions.

Non-diluted fraction II and V and the 1:10 dilution of fraction II were found to inhibit growth of USDA 110 or USDA 123. In all cases, the induction response appeared to saturate at higher concentrations with stronger induction responses observed with increasing dilution of a fraction. This effect may result from saturation of the induction response as a function of inducer concentration or may be due fully or in part to bacterial growth inhibition.

EXAMPLE 5

Induction of Nod—lac fusions by flavones, isoflavones and related compounds

A variety of isoflavones, flavones and related compounds were assayed for nod gene induction activity in both USDA 110 and USDA 123 containing the nod—lac fusions described in Example 2 using the method described in Example 3. Most compounds tested were obtained from commercial sources and were used without further purification. Samples of 7-hydroxyisoflavone, 5,7-dihydroxyflavone, 3',4',7-trihydroxyisoflavone and 3',4',5',7-tetrahydroxyisoflavone (Baptigenin) were provided by Dr. John Norris (University of Texas, Austin). The procedure of Gaydou and Bianchini (1978)

Bull. Soc. Chimi. France 2:43 was used to synthesize 4',7-dihydroxyflavone.

Table 3 presents representative results of *nod* gene induction assays for individual compounds. Included in this Table are assays with both USDA 123 and USDA 110 at two induction times. In each case, the potential inducer was added to the culture at a concentration of 5 $\mu$M at time zero. Induction response was measured as $\beta$-galactosidase activity as defined in Example 3. Since the bacteria continue to grow during the induction period, the data taken at 4 and 21 hr. represent measurements made on bacterial cultures in different growth stages. The data in Table 3 are the mean of three replicates (standard deviation). The compounds tested have been assessed qualitatively as inducers (+), weak inducers (w) or noninducers (−), based on the results in Table 3. A positive induction response corresponds to $\beta$-galactosidase activity at least 4-fold higher than background. A weak response corresponds to enzyme activity at least 2-fold but less than 4-fold over background. A negative response is enzyme activity less than 2-fold over background. A molecule was assessed as an inducer if a positive induction response was observed at either of the induction time points. Weak inducers were assessed in a similar way.

Daidzein, genistein, 7-hydroxyisoflavone, 5,7-dihydroyxisoflavone, biochanin A, 4',7-dihydroxyflavone and apigenin induced a positive response with both strains. Formononetin induced a positive response with USDA 110 and a weak response with USDA 123. Prunetin and kaempferol were weak inducers of both strains, while coumestrol was a weak inducer for strain USDA 110. The isoflavones, baptegenin and 3',4',7-trihydroxyisoflavone displayed no *nod* gene induction response in these experiments. The flavones luteolin, chrysin, naringenin and quercetin did not induce *nod* gene expression in these experiments. In addition, umbelliferone (results in Table 3) and estrone, $\beta$-estradiol, trigonelline and diethylstilbestrol (results not in Table 3) did not induce *nod* gene expression when assayed at 5 $\mu$M level.

Those skilled in the art will appreciate that the invention described herein and the analytical methods, and methods used to isolate, characterize and manipulate DNA specifically described are susceptible to variations and modifications other than as specifically described. It is to be understood that the invention includes all such variations and modifications which fall within its spirit and scope.

We claim:

1. A recombinant DNA molecule comprising a nucleotide sequence of a *nod*D−1 or *nod*D−2 gene of a *Bradyrhizobium japonicum* strain wherein said *Bradyrhizobium japonicum* strain is *Bradyrhizobium japonicum* USDA110 or USDA123.

2. A recombinant DNA molecule comprising a nucleotide sequence of a *nod*D−1 gene of a *Bradyrhizobium japonicum* strain wherein said nucleotide sequence of said *nod*D−1 gene is the *nod*D−1 sequence of FIG. 3.

3. A recombinant DNa molecule comprising a nucleotide sequence of a *nod*D−2 gene of a *Bradyrhizobium japonicum* strain wherein said nucleotide sequence of said *nod*D−2 gene is the *nod*D−2 sequence of FIG. 4.

4. The recombinant DNA molecule of claim 2 wherein the DNA molecule is pEA5-1B.

5. The recombinant DNA molecule of claim 3 wherein the DNA molecule is pRJ103.

* * * * *

UNITED STATES PATENT AND TRADEMARK OFFICE
CERTIFICATE OF CORRECTION

PATENT NO. : 5,023,180

DATED : June 11, 1991

INVENTOR(S) : Appelbaum, Hennecke, Lamb, Gottfert

It is certified that error appears in the above-identified patent and that said Letters Patent is hereby corrected as shown below:

At cover page, first column, 4th line under "PUBLICATIONS", please rewrite "Innes et al.," as --Innes et al.--.

At cover page, first column, 5th line under "PUBLICATIONS", please rewrite "Kondcrosi" as --Kondorosi--.

At cover page, first column, 16th line under "PUBLICATIONS", please rewrite "Gottfert" as --Göttfert--.

column 1, line 17, please rewrite "Rhizobium" as --*Rhizobium*--.

column 1, line 22, please rewrite "Rhizobium" as --*Rhizobium*--.

column 1, line 27, please rewrite "Bradyrhizobium" as --*Bradyrhizobium*--.

column 1, lines 43-45, please rewrite ""Bradyrhizobium sp. (Vigna) and Bradyrhizobium sp. Parasponia" as --*Bradyrhizobium* sp. (*Vigna*) and *Bradyrhizobium* sp. *Parasponia*--.

column 1, line 46, please rewrite "Parasponia" as --*Parasponia*--.

column 1, line 49, please rewrite "USDA110 and USDA123" as --USDA 110 and USDA 123--.

column 1, line 54, please rewrite "USDA110" as --USDA 110--.

UNITED STATES PATENT AND TRADEMARK OFFICE
CERTIFICATE OF CORRECTION

PATENT NO. : 5,023,180

DATED : June 11, 1991

INVENTOR(S) : Appelbaum, Hennecke, Lamb, Gottfert

It is certified that error appears in the above-identified patent and that said Letters Patent is hereby corrected as shown below:

column 1, line 55, please rewrite "USDA123 strains, but USDA123" as --USDA 123 strains, but USDA 123--.

column 1, line 57, please rewrite "USDA110" as --USDA 110--.

column 1, line 61, please rewrite "Rhizobium-legume" as --<u>Rhizobium</u>-legume--.

column 2, line 15, please rewrite "Rhizobium" as --<u>Rhizobium</u>--.

column 2, line 16, please rewrite "Aorobacterium" as --<u>Agrobacterium</u>--.

column 2, line 58, please insert a new paragraph after "for infection.".

column 2, line 66, please rewrite "Gottfert" as --Göttfert--.

column 3, line 3, please rewrite ""R. meliloti" as --<u>R. meliloti</u>--.

column 3, line 11, please rewrite "Rhizobium" as --<u>Rhizobium</u>--.

column 3, line 17, please rewrite "Nod-" as --Nod⁻--.

column 3, line 19, please rewrite "Nod-" as --Nod⁻-- at both instances.

UNITED STATES PATENT AND TRADEMARK OFFICE
CERTIFICATE OF CORRECTION

PATENT NO. : 5,023,180
DATED : June 11, 1991
INVENTOR(S) : Appelbaum, Hennecke, Lamb, Gottfert It is certified that error appears in the above-identified patent and that said Letters Patent is hereby corrected as shown below:

column 3, line 21, please rewrite "Gottfert" as --Göttfert--.

column 3, line 25, please rewrite "0211662 R." as --0211662). R.-- column 3, line 42, please rewrite "(I986)" as --(1986)--.

column 3, line 56, please rewrite "Rhizobium" as --Rhizobium--.

column 3, line 59, please rewrite "Bradyrhizobium" as --Bradyrhizobium--.

column 4, line 6, please rewrite "(Viona)" as --(Vigna)--.

column 4, line 21, please rewrite "Rhizobium" as --Rhizobium--.

column 4, line 61, please rewrite "(I965)" as --(1965)--.

column 5, line 6, please rewrite "1986" as --(1986)--.

column 5, line 8, please rewrite "1985" as --(1985)--.

column 5, line 47, please delete "Schofield et al.,".

UNITED STATES PATENT AND TRADEMARK OFFICE
CERTIFICATE OF CORRECTION

PATENT NO. : 5,023,180

DATED : June 11, 1991

INVENTOR(S) : Appelbaum, Hennecke, Lamb, Gottfert

It is certified that error appears in the above-identified patent and that said Letters Patent is hereby corrected as shown below:

column 5, line 48, please rewrite "(1985" as --(1985)--.

column 5, line 52, please rewrite "Rhizobium" as --Rhizobium--.

column 5, line 55, please rewrite "Rhizobium nodgenes" as --Rhizobium nod genes--.

column 6, line 1, please rewrite "nodgene" as --nod gene--.

column 6, line 6, please rewrite "nodgene" as --nod gene--.

column 6, line 20, please rewrite "apigenineriodict" as --apingenin--.

column 6, line 29, please rewrite "Vicia sativa" as --Vicia sativa--.

column 6, line 32, please rewrite "nodgene" as --nod gene--.

column 6, line 42, please rewrite "nodgene" as --nod gene--.

column 6, line 44, please rewrite "A;" as --A,--.

column 6, line 47, please rewrite "nodgene" as --nod gene--.

UNITED STATES PATENT AND TRADEMARK OFFICE
CERTIFICATE OF CORRECTION

PATENT NO. : 5,023,180

DATED : June 11, 1991

INVENTOR(S) : Appelbaum, Hennecke, Lamb, Gottfert

It is certified that error appears in the above-identified patent and that said Letters Patent is hereby corrected as shown below:

column 6, line 49, please rewrite "Rhizobium" as --*Rhizobium*--.

column 6, line 51, please rewrite "nodgene" as --*nod* gene--.

column 6, line 55, please rewrite "Bradyrhizobium sp. Parasponia" as --*Bradyrhizobium* sp. *Parasponia*--.

column 6, line 58, please rewrite "nodgene" as --*nod* gene--.

column 6, line 59, please rewrite "Rhizobium" as --*Rhizobium*--.

column 6, bridging lines 59 and 60, please rewrite "Rhizobium" as --*Rhizobium*--.

column 7, line 13, please rewrite "nodprotein" as --*nod* protein--.

column 7, line 58, please rewrite "Rhizobium and Bradyrhizobium" as --*Rhizobium* and *Bradyrhizobium*--.

column 8, lines 22 and 23, please rewrite "nodgene" as --*nod* gene--.

column 8, line 25, please rewrite "abandoned filed" as --abandoned, filed--.

column 8, bridging lines 48 & 49, please rewrite "Rhizobium or Bradyrhizobium" as --*Rhizobium* or *Bradyrhizobium*--.

UNITED STATES PATENT AND TRADEMARK OFFICE
CERTIFICATE OF CORRECTION

PATENT NO. : 5,023,180

DATED : June 11, 1991

INVENTOR(S) : Appelbaum, Hennecke, Lamb, Gottfert

It is certified that error appears in the above-identified patent and that said Letters Patent is hereby corrected as shown below:

column 8, bridging lines 58 & 59, please rewrite "USDA123" as --USDA 123--.

column 8, line 60, please rewrite "_nod_genes" as --_nod_ genes--.

column 9, bridging lines 1 & 2, please rewrite "USDA110" as --USDA 110--.

column 9, lines 5 and 6, please rewrite "USDA110" as --USDA 110--.

column 9, lines 6 and 7, please rewrite "USDA123" as --USDA 123--.

column 9, line 8, please rewrite "USDA110" as --USDA 110--.

column 9, line 31, please rewrite "_nod_D-1" as --_nod_D-1's--.

column 9, line 48, please rewrite "_sequences (R.f._" without italics.

column 9, line 52, please rewrite "Gottfert" as --Göttfert--.

column 9, line 58, please rewrite "Rhizobium" as --_Rhizobium_--.

column 10, line 2, please rewrite "abandoned filed" as --abandoned, filed--.

UNITED STATES PATENT AND TRADEMARK OFFICE
CERTIFICATE OF CORRECTION

PATENT NO. : 5,023,180
DATED : June 11, 1991
INVENTOR(S) : Appelbaum, Hennecke, Lamb, Gottfert It is certified that error appears in the above-identified patent and that said Letters Patent is hereby corrected as shown below:

column 10, line 15, please rewrite "Rhizobium" as --*Rhizobium*--.

column 10, bridging lines 15-16, please rewrite "Bradyrhizobium" as --*Bradyrhizobium*--.

column 10, line 59, please rewrite "upstream" as --downstream--.

column 11, bridging lines 63-64, please rewrite "Rhizobium" as --*Rhizobium*--.

column 13, line 21, please rewrite "Rhizobium and Bradyrhizobium" as --*Rhizobium* and *Bradyrhizobium*--.

column 13, lines 24 and 33, please rewrite "nodgenes" as --*nod* genes--.

column 13, bridging lines 39 & 40, please rewrite "Rhizobium" as --*Rhizobium*--.

column 13, bridging lines 43 & 44, please rewrite "Bradyrhizobium" as --*Bradyrhizobium*--.

column 13, line 46, please rewrite "7,4-dihydroxyflavone" as --4',7-dihydroxyflavone--.

column 13, bridging lines 47-48, please rewrite "*lac*fusions" as --*lac* fusions--.

column 13, line 52, please rewrite "*nod*gene" as --*nod* gene--.

UNITED STATES PATENT AND TRADEMARK OFFICE
CERTIFICATE OF CORRECTION

PATENT NO. : 5,023,180

DATED : June 11, 1991

INVENTOR(S) : Appelbaum, Hennecke, Lamb, Gottfert

It is certified that error appears in the above-identified patent and that said Letters Patent is hereby corrected as shown below:

column 13, line 61, please rewrite "nodgene" as --nod gene--.

column 14, line 45, please rewrite "USDA123" as --USDA 123--.

column 14, line 49, please rewrite "USDA110" as --USDA 110--.

column 14, line 57, please rewrite "USDA110" as --USDA 110--.

column 15, line 3, please rewrite "Bradyrhizobium" as --Bradyrhizobium--.

column 15, line 4, please rewrite "(Parasponia)" as --(Parasponia)--.

column 15, line 14, please rewrite "USDA110" as --USDA 110--.

column 15, line 23, please rewrite "USDA123" as --USDA 123--.

column 15, line 31, please rewrite "nod-box" as --nod-box--.

column 15, line 33, please rewrite "USDA123" as --USDA 123--.

column 15, line 37, please rewrite "USDA123" as --USDA 123--.

UNITED STATES PATENT AND TRADEMARK OFFICE
CERTIFICATE OF CORRECTION

PATENT NO. : 5,023,180

DATED : June 11, 1991

INVENTOR(S) : Appelbaum, Hennecke, Lamb, Gottfert

It is certified that error appears in the above-identified patent and that said Letters Patent is hereby corrected as shown below:

column 15, line 39, please rewrite "USDA110" as --USDA 110--.

column 15, line 43, please rewrite "USDA110" as --USDA 110--.

column 15, line 45, please rewrite "USDA123" as --USDA 123--.

column 15, line 46, please rewrite "USDA110" as --USDA 110--.

At page 8, column 15, line 49, please rewrite "USDA110" as --USDA 110--.

column 15, line 50, please rewrite "USDA110" as --USDA 110-- in both occurrences.

column 15, line 52, please rewrite "USDA123" as --USDA 123--.

column 15, line 56, please rewrite "USDA123" as --USDA 123--.

column 15, line 57, please rewrite "USDA110" as --USDA 110--.

column 15, line 64, please rewrite "mobilized, by" as --modilized by--.

column 15, line 65, please rewrite "USDA110" as --USDA 110--.

UNITED STATES PATENT AND TRADEMARK OFFICE
CERTIFICATE OF CORRECTION

PATENT NO. : 5,023,180
DATED : June 11, 1991
INVENTOR(S) : Appelbaum, Hennecke, Lamb, Gottfert It is certified that error appears in the above-identified patent and that said Letters Patent is hereby corrected as shown below:

column 16, line 22, please rewrite "the ( N" as --the N--.

column 16, bridging lines 24-25, please rewrite "Bradyrhizobium and Rhizobium" as --*Bradyrhizobium* and *Rhizobium*--.

column 16, line 28, please rewrite "C-terminal" as --C-terminus--.

column 16, bridging lines 49-50, please rewrite "sequences divergence near 10 the" as --sequence divergence near the--.

column 16, line 55, please rewrite "Rhizobium" as --*Rhizobium*--.

column 16, bridging lines 60-61 and 63-64, please rewrite "Bradyrhizobium sp. Parasponia" as --*Bradyrhizobium* sp. *Parasponia*--.

column 16, line 68, please rewrite "Bradyrhizobium" as --*Bradyrhizobium*--.

column 17, line 2, please rewrite "Rhizobium" as --*Rhizobium*--.

column 17, line 3, please rewrite "Bradyrhizobium" as --*Bradyrhizobium*--.

column 17, line 7, please rewrite "Bradyrhizobium sp. Parasponia)" as --*Bradyrhizobium* sp. *Parasponia*--.

UNITED STATES PATENT AND TRADEMARK OFFICE
CERTIFICATE OF CORRECTION

PATENT NO. : 5,023,180

DATED : June 11, 1991

INVENTOR(S) : Appelbaum, Hennecke, Lamb, Gottfert

It is certified that error appears in the above-identified patent and that said Letters Patent is hereby corrected as shown below:

column 17, bridging lines 11 & 12, please rewrite "Bradyrhizobium sp. Parasponia" as --*Bradyrhizobium* sp. Parasponia--.

column 17, line 13, please rewrite "Bradyrhizobium" as --*Bradyrhizobium*--.

column 17, line 34, please rewrite "*b*. *japonicum* 286 nodulation" as --*B*. *japonicum* nodulation--.

At page 9, column 17, line 41, please rewrite "Leoume" as --Legume--.

column 17, line 65, please rewrite "Rhizobium, Bradyrhizobium" as --*Rhizobium*, *Bradyrhizobium*--.

column 17, line 66, please rewrite "Agrobacterium" as --*Agrobacterium*--.

column 18, line 21, please rewrite "et al (1985) supra" as --et al. (1985) *supra*--.

column 18, line 60, please rewrite "10 protein of Bacillus thuringiensis" as --protein of *Bacillus thuringiensis*--.

column 19, line 10, please rewrite "Bradyrhizobium USDA123" as --*Bradyrhizobium* USDA 123--.

column 19, line 11, please rewrite "USDA123" as --USDA 123--.

UNITED STATES PATENT AND TRADEMARK OFFICE
CERTIFICATE OF CORRECTION

PATENT NO. : 5,023,180  Page 12 of 18
DATED : June 11, 1991
INVENTOR(S) : Appelbaum, Hennecke, Lamb, Gottfert It is certified that error appears in the above-identified patent and that said Letters Patent is hereby corrected as shown below:

column 19, line 13, please rewrite "USDA123" as --USDA 123--.

column 19, line 14, please rewrite "USDA123" as --USDA 123--.

column 19, line 19, please rewrite "USDA123" as --USDA 123--.

column 19, line 27, please rewrite "USDA191" as --USDA 191-- column 19, bridging lines 27 & 28, please rewrite "Appelbaum et al." as --(Appelbaum et al.--.

column 19, bridging lines 30 & 31, please rewrite "USDA123" as --USDA 123--.

column 19, line 34, please rewrite "USDA123" as --USDA 123--.

column 19, line 36, please rewrite "USDA123" as --USDA 123--.

column 19, line 37, please rewrite "USDA123" as --USDA 123--.

column 19, line 41, please rewrite "USDA123" as --USDA 123--.

column 19, line 42, please rewrite "soc" as --spc--

UNITED STATES PATENT AND TRADEMARK OFFICE
CERTIFICATE OF CORRECTION

PATENT NO. : 5,023,180
DATED : June 11, 1991
INVENTOR(S) : Appelbaum, Hennecke, Lamb, Gottfert It is certified that error appears in the above-identified patent and that said Letters Patent is hereby corrected as shown below:

column 19, line 50, please rewrite "USDA123" as --USDA 123--.

column 19, line 56, please rewrite "1.5$_7$" as --1.5--.

column 19, line 62, please rewrite "fragment This" as --fragment. This--.

column 19, line 67, please rewrite "USDA123" as --USDA 123--.

column 19, line 68, please rewrite "procedure (Maniatis, 1982). Again" as --procedures (Maniatis, 1982). Again,-- column 20, line 7, please rewrite "USDA123" as --USDA 123--.

column 20, line 13, please rewrite "inserts; while" as --inserts, while--.

column 20, line 21, please rewrite "*strain*" without italics.

column 20, line 22, please rewrite "USDA191" as --USDA 191--.

column 21, line 25, please rewrite "(Schofield and Watson," without italics.

column 21, line 25, please rewrite "Bradyrhizobium" as --<u>Bradyrhizobium</u>--.

UNITED STATES PATENT AND TRADEMARK OFFICE
CERTIFICATE OF CORRECTION

PATENT NO. : 5,023,180

DATED : June 11, 1991

INVENTOR(S) : Appelbaum, Hennecke, Lamb, Gottfert

It is certified that error appears in the above-identified patent and that said Letters Patent is hereby corrected as shown below:

column 21, line 26, please rewrite "Parasponia" as --*Parasponia*--.

column 21, line 26, please rewrite "(1986)Nucleic" as --(1986) Nucleic--.

column 21, line 27, please rewrite "2919 and" as --2919) and--.

column 21, line 29, please rewrite "European Publication No. 0211662" as --(European Publication No. 0211662)--.

column 21, line 54, please rewrite "nodgene" as --*nod* gene--.

column 22, line 28, please rewrite "nodgene" as --*nod* gene--.

column 22, line 29, please rewrite "et al" as --et al.--.

column 22, line 35, please rewrite "Bol" as --Bgl-- column 22, line 57, please rewrite "Bradyrhizobium" as --*Bradyrhizobium*--.

column 22, line 59, please rewrite "Bradyrhizobium" as --*Bradyrhizobium*--.

column 22, bridging lines 66 & 67, please rewrite "Bradyrhizobium" as --*Bradyrhizobium*--.

UNITED STATES PATENT AND TRADEMARK OFFICE
CERTIFICATE OF CORRECTION

PATENT NO. : 5,023,180

Page 15 of 18

DATED : June 11, 1991

INVENTOR(S) : Appelbaum, Hennecke, Lamb, Gottfert

It is certified that error appears in the above-identified patent and that said Letters Patent is hereby corrected as shown below:

column 23, line 4, please rewrite "USDA123" as --USDA 123--.

column 23, lines 5 & 6, please rewrite "USDA123 spc and USDA 110" as --USDA 123 spc and USDA 110--.

At page 12, column 23, line 8, please rewrite "USDA123" as --USDA 123--.

column 23, line 9, please rewrite "nod- deletion" as --nod- deletion--.

column 23, line 29, please rewrite "$\mu$-galactosidase" as --ß-galactosidase--.

column 23, line 60, please rewrite "27.C" as --27°C--.

column 24, line 3, please rewrite "(3x)" as --(3X)--.

column 25, line 26, please rewrite "Daidze in" as --Daidzein-- column 25, line 33, please rewrite "baptegenin" as --baptigenin--.

column 26, line 26, claim 3, please rewrite "DNa" as --DNA--.

Tables 1-3, should be added as shown on the attached pages.

Table 1: Amino Acid Abbreviations

| | |
|---|---|
| A = Ala = Alanine | M = Met = Methionine |
| C = Cys = Cysteine | N = Asn = Asparagine |
| D = Asp = Aspartic Acid | P = Pro = Proline |
| E = Glu = Glutamic Acid | Q = Gln = Glutamine |
| F = Phe = Phenylalanine | R = Arg = Arginine |
| G = Gly = Glycine | S = Ser = Serine |
| H = His = Histidine | T = Thr = Threonine |
| I = Ile = Isoleucine | V = Val = Valine |
| K = Lys = Lysine | W = Trp = Tryptophan |
| L = Leu = Leucine | Y = Tyr = Tyrosine |

Table 2: <u>Nod</u> Gene Induction Activity of Soybean Exudate Fractions $\beta$-galactosidase Activity (Normalized Units[1])

| Fraction[2] (concentration (mg/l) or dilution) | Strain: USDA 110 | USDA 123 |
|---|---|---|
| I (38.9) | 2 ± 28% | -- |
| (1:10) | 14 ± 3% | 24 ± 14% |
| (1:100) | 86 ± 3% | 172 ± 9% |
| (1:1000) | -- | 334 ± 14% |
| II (0.398) | inhibited growth | -- |
| (1:10) | 1268 ± 7% | inhibited growth |
| (1:100) | 9422 ± 9% | 22,236 ± 11% |
| (1:1000) | -- | 50,251 ± 19% |
| III (41.06) | 1 ± 15% | -- |
| (1:10) | 12 ± 6% | 24 ± 45% |
| (1:100) | 35 ± 5% | 22 ± 10% |
| (1:1000) | -- | 98 ± 20% |
| IV (29.1) | -- | -- |
| (1:10) | 3 ± 7% | 16 ± 2% |
| (1:100) | 9 ± 12% | 14 ± 20% |
| V (0.28) | inhibited growth | -- |
| (1:10) | 1732 ± 7% | 2804 ± 12% |
| (1:100) | 12,679 ± 7% | 47,857 ± 8% |
| (1:1000) | -- | 42,857 ± 15% |

[1] $\beta$-galactosidase activity was measured as described in Example 3, with an induction time of 18-21 hours. Specific activity (-background) was normalized for fraction concentration in mg/ml to allow comparison of different fractions. The values are the mean ± standard deviation (%) of three replicate samples.

[2] Fractions are as described in Example 4.

Table 3: *B. japonicum* Nod Gene Induction Response

| Compounds | USDA 110 2 hrs | | 4 hrs | | USDA 123 2 hrs | | 4 hrs | |
|---|---|---|---|---|---|---|---|---|
| Background | 10±3 | | (9±0) | | 8±5 | | (10±3) | |
| Soybean Root Exudate (fraction I)[2] | 72±20 | + | (ND) | | 95±13 | + | (ND) | |
| Isoflavones | | | | | | | | |
| Daidzein | 63±6 | + | (51±2) | + | 76±8 | + | (56±8) | + |
| Genistein | 67±5 | + | (61±5) | + | 65±2 | + | (76±11) | + |
| 7-hydroxyisoflavone | 56±4 | + | (56±5) | + | 69±2 | + | (12±4) | - |
| 5,7-hydroxyisoflavone | 68±5 | + | (70±5) | + | 110±16 | + | (68±13) | + |
| Baptigenin | 12±1 | - | (ND) | | 11±1 | - | (ND) | |
| 3',4',7-trihydroxyisoflavone | 14±1 | - | (ND) | | 9±1 | - | (ND) | |
| Biochanin A | 37±3 | + | (61±6) | + | 14±2 | - | (51±12) | + |
| Formononetin | 19±5 | - | (35±9) | + | 11±1 | - | (22±4) | w |
| Prunetin | 20±2 | w | (28±3) | w | 20±3 | w | (12±2) | - |
| Flavones | | | | | | | | |
| 4',7-dihydroxyflavone | 43±4 | + | (57±4) | + | 30±4 | + | (52±6) | + |
| Apigenin | 21±2 | w | (43±11) | + | 38±12 | + | (68±9) | + |
| Luteolin | 7±1 | - | (14±2) | - | 4±1 | - | (15±1) | - |
| Chrysin | 6±10 | - | (12±1) | - | 7±1 | - | (13±3) | - |
| Flavanone/Flavonols | | | | | | | | |
| Naringenin | 8±10 | - | (12±1) | - | 4±1 | - | (13±3) | - |
| Quercetin | 7±1 | - | (11±1) | - | 4±1 | - | (11±2) | - |
| Kaempferol | 20±2 | w | (18±3) | w | 18±9 | w | (12±1) | - |
| Coumestans | | | | | | | | |
| Coumestrol | 27±4 | w | (22±1) | w | 13±2 | - | (19±3) | - |
| Umbelliferone | 8±1 | - | (10±1) | - | 4±1 | - | (12±1) | - |

1  In all cases the *B. japonicum* strain contains the nodC-lacZ fusion plasmid pEA2-21; Induction response is measured as β-galactosidase activity (Example 2); + = activity 4-fold over background; w (weak) = activity at least 2-fold but less than 4-fold over background; - = activity less than 2-fold over background
2  Preparation of soybean exudate fraction is described in Example 4.